United States Patent
Rowland et al.

(10) Patent No.: US 11,103,202 B2
(45) Date of Patent: Aug. 31, 2021

(54) MOBILE RADIOGRAPHIC IMAGING APPARATUS HAVING COUNTERBALANCED SLEWABLE ARM

(71) Applicant: MICRO-X Limited, Tonsley (AU)

(72) Inventors: Peter Rowland, Tonsley (AU); Richard Byers, Tonsley (AU); Anthony Skeats, Tonsley (AU); Chin Eng Yeap, Tonsley (AU)

(73) Assignee: MICRO-X LIMITED, Tonsley (AU)

( * ) Notice: Subject to any disclaimer, the term of this patent is extended or adjusted under 35 U.S.C. 154(b) by 234 days.

(21) Appl. No.: 15/770,129

(22) PCT Filed: Oct. 21, 2016

(86) PCT No.: PCT/AU2016/050993
§ 371 (c)(1),
(2) Date: Apr. 20, 2018

(87) PCT Pub. No.: WO2017/066841
PCT Pub. Date: Apr. 27, 2017

(65) Prior Publication Data
US 2018/0310902 A1    Nov. 1, 2018

(30) Foreign Application Priority Data
Oct. 21, 2015  (AU) ................................ 2015904310

(51) Int. Cl.
*A61B 6/00*      (2006.01)
*F16M 11/42*    (2006.01)
(Continued)

(52) U.S. Cl.
CPC .......... *A61B 6/4405* (2013.01); *A61B 6/4411* (2013.01); *A61B 6/4429* (2013.01);
(Continued)

(58) Field of Classification Search
CPC ........... A61B 6/40; A61B 6/44; A61B 6/4405; A61B 6/4411; A61B 6/4429;
(Continued)

(56) References Cited

U.S. PATENT DOCUMENTS

| | | | |
|---|---|---|---|
| 1,600,867 | A | 9/1926 | Coolidge |
| 2,036,097 | A | 3/1936 | Pieper |

(Continued)

FOREIGN PATENT DOCUMENTS

| | | | | |
|---|---|---|---|---|
| AU | 741567 | B2 | 12/2001 | |
| CA | 2877381 | A1 * | 1/2015 | ............... A61B 6/10 |

(Continued)

*Primary Examiner* — Anastasia Midkiff
(74) *Attorney, Agent, or Firm* — Seed IP Law Group LLP

(57) ABSTRACT

There is disclosed a mobile radiographic imaging apparatus including a component operable to emit radiation for imaging a subject, an arm rotatably connected at a proximal end thereof to a body section of the apparatus, such that it is supported by the body section and can slew relative to the body section about an upright axis, and to a distal end of which said component is connected, and a generator assembly arranged in the body section and including a generator arranged in the casing and electrically connected to said component, the apparatus being configured such that the generator assembly rotates with the arm, about said axis, wherein the generator assembly has a centre of mass which is radially offset from said axis in a second direction that is substantially opposite to said first direction.

7 Claims, 36 Drawing Sheets

(51) Int. Cl.
*F16M 11/18* (2006.01)
*A61B 90/50* (2016.01)
*A61B 34/30* (2016.01)
*F16M 11/08* (2006.01)
*F16M 11/12* (2006.01)
*F16M 11/20* (2006.01)
*H05G 1/02* (2006.01)

(52) U.S. Cl.
CPC .......... *A61B 6/4458* (2013.01); *A61B 6/4476* (2013.01); *A61B 6/587* (2013.01); *A61B 6/588* (2013.01); *A61B 90/50* (2016.02); *F16M 11/18* (2013.01); *F16M 11/42* (2013.01); *A61B 6/405* (2013.01); *A61B 34/30* (2016.02); *A61B 2034/305* (2016.02); *A61B 2090/504* (2016.02); *A61B 2090/5025* (2016.02); *A61B 2560/0431* (2013.01); *F16M 11/08* (2013.01); *F16M 11/12* (2013.01); *F16M 11/125* (2013.01); *F16M 11/2064* (2013.01); *F16M 2200/041* (2013.01); *F16M 2200/068* (2013.01); *G01N 2223/301* (2013.01); *G01N 2223/308* (2013.01); *G01N 2223/321* (2013.01); *H05G 1/02* (2013.01)

(58) Field of Classification Search
CPC ..... A61B 6/4458; A61B 6/4476; A61B 6/587; A61B 6/588; A61B 6/589; A61B 34/30; A61B 90/50; A61B 2034/305; A61B 2090/5025; A61B 2090/504; A61B 2560/02; A61B 2560/04; A61B 2560/0431; G01N 2223/30; G01N 2223/301; G01N 2223/308; G01N 2223/32; G01N 2223/321; H01J 2235/00; H01J 2235/02; H01J 2235/023; H05G 1/02; F16M 11/02; F16M 11/04; F16M 11/06; F16M 11/08; F16M 11/10; F16M 11/12; F16M 11/18; F16M 11/42; F16M 2200/04; F16M 2200/041; F16M 2200/06; F16M 2200/066

See application file for complete search history.

(56) References Cited

U.S. PATENT DOCUMENTS

| | | |
|---|---|---|
| 2,125,586 A | 8/1938 | Pohl |
| 3,025,401 A | 3/1962 | Lauterbach |
| 4,166,602 A | 9/1979 | Nilsen et al. |
| 4,625,116 A | 11/1986 | Hanz et al. |
| 4,692,625 A | 9/1987 | Hanz et al. |
| 7,887,236 B2 | 2/2011 | Dehler et al. |
| 2013/0129048 A1 | 5/2013 | Chicchetti et al. |
| 2014/0369459 A1 | 12/2014 | Foos et al. |
| 2015/0043712 A1 | 2/2015 | Wang et al. |
| 2015/0265223 A1 | 9/2015 | Simon et al. |
| 2016/0181053 A1 | 6/2016 | Wang et al. |
| 2016/0256128 A1 | 9/2016 | Wang et al. |
| 2017/0020479 A1 | 1/2017 | Shimohira |

FOREIGN PATENT DOCUMENTS

| | | |
|---|---|---|
| GB | 786636 A | 11/1957 |
| WO | 2015/018848 A2 | 2/2015 |

\* cited by examiner

MOBILE RADIOGRAPHIC IMAGING APPARATUS HAVING COUNTERBALANCED SLEWABLE ARM

FIELD OF THE INVENTION

The present invention relates to, inter alia, a medical apparatus and components of the apparatus. The invention has particular application to mobile apparatuses and/or radiographic imaging apparatuses, including X-ray apparatuses.

BACKGROUND

Currently in the art, radiographic imaging apparatuses which are intended to be "portable", including in particular, mobile x-ray apparatuses, are generally cumbersome and heavy (typically weighing hundreds of kilograms).

It is desirable in the art to provide a portable radiographic imaging apparatus, as well as componentry for such an apparatus, which is relatively lightweight, easy to operate, safe and reliable.

SUMMARY OF THE INVENTION

According to a first aspect of the present invention, there is provided a mobile radiographic imaging apparatus comprising:
a body section;
ground-engaging wheels arranged to support the body section over a floor surface and permitting manoeuvring of the apparatus over the surface;
a component operable to emit radiation for imaging a subject;
an arm rotatably connected at a proximal end thereof to the body section, such that it is supported by the body section and can slew relative to the body section about an upright axis, and to a distal end of which said component is connected so as to be supported from the support structure via said arm at a position which is radially offset from the axis in a first direction; and
a generator assembly arranged in the body section, the assembly including a generator arranged in the casing and electrically connected to said component to power generation of the radiation by the component,
the apparatus being configured such that the generator assembly rotates with the arm, about said upright axis, during slewing of the arm,
wherein the generator assembly has a centre of mass which is radially offset from said axis in a second direction that is substantially opposite to said first direction, so as to counteract a moment exerted on the body section by said arm and said component.

Preferably, the generator includes a tank of oil having a centre of mass which is radially offset from said axis in said second direction.

Preferably, the generator assembly includes an exterior casing in which the generator is housed. Preferably, the apparatus includes cabling and/or other componentry housed by said casing.

Preferably, the generator assembly is housed by the body section.

Preferably, the proximal end of the arm is connected to the generator assembly such that the rotation of the assembly with the arm during slewing of the arm is enabled. Preferably, the generator assembly hangs or depends from the proximal end of the arm.

Preferably, the apparatus includes a slew bearing having fixed part mounted to the body section and a rotatable part to which the arm is mounted so as to be able to slew about said axis, and the generator assembly is coupled to said rotatable part such that most or all of the weight of the generator assembly is transferred through the slew bearing into the body section.

Preferably, the arm is configured to articulate about at least one axis which is perpendicular to the upright axis and to the first and second directions, whereby a translational position of the component relative to the body section is adjustable.

Preferably, the arm is articulated and said component comprises an X-ray head which the arm suspends from a support section of the apparatus, the arm comprising:
a proximal arm section comprising a first elongate linkage ("the first proximal linkage") and a second elongate linkage ("the second proximal linkage") a proximal end of each of which is connected to the support section such that the first and second proximal linkages are pivotable, relative to the support section, about respective axes which are parallel;
an intermediate linkage to which a distal end of each of the first and second proximal linkages is connected such that the intermediate linkage is pivotable, relative to the first and second elongate linkages about respective axes which are parallel to the axes about which the proximal linkages are pivotable;
a distal arm section comprising a first elongate linkage ("the first distal linkage") and a second elongate linkage ("the second distal linkage") a proximal end of each of which is connected to the intermediate linkage such that the first and second distal linkages are pivotable, relative to the intermediate linkage, about respective axes which are parallel to the axes about which the proximal linkages are pivotable, a distal end of each of the distal linkages being connected to the X-ray head, via a mounting, such that the mounting is pivotable, relative to the first and second distal linkages, about respective axes which are parallel to the axes about which the proximal linkages are pivotable,
whereby, a rotational orientation of the mounting about an axis which is parallel to the axes about which the proximal linkages are pivotable remains constant when the proximal arm section is pivoted or rotated relative to the support section and/or the distal arm section is pivoted or rotated relative to the intermediate linkage in the apparatus.

Preferably, the arm is configured such that the proximal linkages remain parallel when the proximal arm section is pivoted or rotated relative to the support section, and the distal linkages remain parallel when the distal arm section is pivoted or rotated relative to the intermediate linkage.

Preferably, the distal ends of the proximal linkages are connected to a proximal end of the intermediate linkage, and the proximal ends of the distal linkage are connected to a distal end of the intermediate linkage, such that:
the intermediate linkage is pivotable or rotatable relative to the proximal arm section between a first position, relative to the proximal arm section, in which an axis extending from the proximal end of the intermediate linkage to a distal end of the intermediate linkage ("the intermediate linkage axis") extends transverse to a longitudinal axis of the proximal arm section, and a second position, relative to the proximal arm section, in which the intermediate linkage axis extends generally parallel to, or in general alignment with, the longitudinal axis of the proximal arm section; and the distal arm section is pivotable or rotatable relative to the intermediate linkage between a first position, relative to the intermediate linkage, in which a longitudinal axis of the distal arm section extends transverse to the intermediate linkage axis, and a second position, relative to the intermediate linkage, in which the longitudinal axis of the distal arm section extends generally parallel to, or in general alignment with, the intermediate linkage axis, whereby:

when the intermediate linkage and distal arm section assume their first positions, the arm assumes a fully collapsed condition in which the proximal and distal arm sections are positioned in generally side-by-side relation; and when the intermediate linkage and distal arm section assume their second positions, the arm assumes a fully extended condition in which the proximal and distal arm sections are positioned in generally coaxial relation.

Preferably, the apparatus is an X-ray trolley or cart.

Preferably, the mounting is configured to permit rotation of the head relative to the distal ends of the distal linkages about an axis which is perpendicular to the axes about which the proximal linkages are pivotable.

Preferably, the apparatus is configured such that said axis which is perpendicular is parallel to a floor surface when the support structure is supported on the floor surface.

Preferably, the mounting is configured to permit pivoting of the head relative to the distal ends of the distal linkages about an axis which is parallel to the axes about which the proximal linkages are pivotable.

According to a preferred embodiment of the invention, the apparatus includes a braking system, arranged to brake at least one of the wheels, and a grip configured with at least one actuator arranged such that it can be engaged by a hand of the person grasping the grip so as to disengage the braking system, whereupon the person can manoeuvre the apparatus over the ground via the grip with said hand.

Preferably, the apparatus comprises, in addition to said grip ("the first grip"), a further grip ("the second grip"), the second grip being arranged such that it can be grasped by the person's other hand whereby the person can manoeuvre the apparatus over the ground via the first and second grips simultaneously.

Preferably, the second grip is configured with at least one actuator arranged such that it can be engaged by said other hand so as to disengage the braking system, whereupon the person can manoeuvre the apparatus over the ground via the second grip with said other hand.

Preferably, the or each grip is configured in the form of a knob.

Preferably, the or each grip is substantially ball-shaped.

Preferably, the or each actuator of the or each grip configured with at least one actuator comprises a button.

Preferably, a said actuator of the or each grip configured with at least one said actuator is engageable by the palm of the hand which grasps that grip.

Preferably, the or each palm-engageable actuator extends substantially through at least one arc, the or each arc being orientated so as to follow a respective arch of the hand grasping that grip.

In a preferred embodiment of the invention, the or each palm-engageable actuator extends substantially through an arc orientated so as to follow a transverse arch of the hand grasping the grip configured with that actuator, the arc preferably subtending an angle of at least about 90 degrees, the arc more preferably subtending an angle of between about 90 degrees and about 150 degrees, the arc more preferably subtending an angle of about 120 degrees.

In a preferred embodiment of the invention, the or each palm-engageable actuator extends substantially through an arc orientated so as to follow the proximal transverse arch of the hand grasping the grip configured with that actuator, the arc preferably subtending an angle of at least about 75 degrees, the arc more preferably subtending an angle of between about 75 degrees and about 165 degrees, the arc more preferably subtending an angle of about 120 degrees.

Preferably, the or each palm-engageable actuator extends substantially through an arc orientated so as to follow the distal transverse arch of the hand grasping the grip configured with that actuator.

In a preferred embodiment of the invention, the or each palm-engageable actuator extends substantially through an arc orientated so as to follow the longitudinal arch of the hand grasping the grip configured with that actuator, the arc preferably subtending an angle of at least about 75 degrees, the arc more preferably subtending an angle of between about 75 degrees and about 165 degrees, the arc more preferably subtending an angle of about 120 degrees.

Preferably, a said actuator of the or each grip configured with at least one said actuator is engageable by at least one digit of the hand which grasps that grip.

Preferably, the or each digit-engageable actuator is engageable by at least one finger of the hand which grasps the grip configured with that actuator.

Preferably, the or each digit-engageable actuator is engageable by the tip of at least one digit of the hand which grasps the grip configured with that actuator.

Preferably, the or each digit-engageable actuator is engageable by the pad of the tip of at least one digit of the hand which grasps the grip configured with that actuator.

Preferably, the or each digit-engageable actuator is orientated to extend transverse to digits of the hand which grasps the grip configured with that actuator, such that it can be engaged by plural digits of that hand. In a preferred embodiment of the invention, the or each digit-engageable actuator extends substantially through an arc such that it can be engaged by said plural digits, the arc preferably subtending an angle of at least about 45 degrees, the arc more preferably subtending an angle of between about 45 degrees and about 95 degrees, the arc more preferably subtending an angle of about 70 degrees.

Preferably, the or each grip configured with at least one actuator is configured with opposed said actuators.

Preferably, the or each grip configured with at least one actuator is attached to the rest of the apparatus at a bottom part of that grip.

Preferably, the or each grip configured with at least one actuator is arranged at an end of a respective handle of the apparatus. Preferably, the or each handle comprises an upwardly projecting arm to an upper end of which the respective grip is attached.

Preferably, the or each grip is arranged at a rear of the apparatus such that the apparatus can be pushed forwardly over the ground by the person standing at said rear and pushing on the grip(s) with either or each of his or her hands engaging at least one said actuator.

According to a preferred embodiment of the present invention, the X-ray head includes:

a main body which includes a source of radiation;

a collimator operable to adjust the size of an aperture in the main body and thus one or more transverse dimensions of a beam of the radiation emittable from the main body section, along an axis, for imaging a subject; and a pair of handles, the handles being spaced apart and projecting from the main body in a direction substantially parallel to the axis, the handles being graspable by respective hands of an operator whereby the component can be manipulated to orientate the beam, wherein either or each of the handles is configured with an adjustor which is manually operable to effect adjustment of the aperture size.

Preferably, the handles are configured in the form of tusks.

Preferably, the main body includes a window arranged such that said beam is emitted therethrough and the handles are arranged at opposite lateral sides of the window.

Preferably, each handle is configured with a said adjustor, and wherein the adjustors are operable to adjust respective dimensions of the aperture which are mutually perpendicular.

Preferably, the or each adjustor is arranged at a distal end of the handle which is configured therewith.

Preferably, the or each adjustor is rotatable to effect adjustment of the aperture size.

Preferably, the or each adjustor is rotatable about a longitudinal axis of the handle configured therewith, to effect adjustment of the aperture size.

Preferably, the handles are arranged such that distal ends thereof lie in a plane which is orthogonal to said axis and spaced from a focal spot of the radiation source by at least a predetermined distance.

Preferably, the pair of handles is supported from the main body in a manner permitting said pair to rotate about an axis which is parallel to the beam axis, whereby the pair of handles is turnable to effect adjustment of a rotational orientation of the aperture about the axis of rotation.

Preferably, the X-ray head includes a light source arranged to emit light through the aperture such that a resulting light beam from the aperture, when incident on a surface remote from the component and faced by the aperture, illuminates an area of the surface over or within which said imaging is effected, and either or each handle is configured with a switch manually operable to turn the light source on and/or off. Preferably, the or each switch is arranged at a distal end of the handle configured therewith.

Preferably, the X-ray head comprises:
a support section;
a source of radiation held by the support section;
a collimator operable to adjust the size of an aperture of the component and thus one or more transverse dimensions of a beam of the radiation emittable from the head for imaging a subject; and
a backscatter shield which is made of a composite material comprising tungsten powder and a polymeric binder, and arranged to absorb radiation from the source that is reflected by the collimator,
the collimator being supported from the support section via the shield.

Preferably, the shield is moulded from said material.

Preferably, the shield is injection moulded from said material.

Preferably, the shield is formed as a single piece.

Preferably, the shield comprises a side wall which bounds an interior of the shield and is formed with an opening therethrough to admit, into the interior, visible light from a light source of the X-ray head for illuminating on a subject a target site where a radiographic image is to be taken by the apparatus.

Preferably, a mirror is supported from the side wall in said interior to direct said light towards the collimator.

Preferably, the shield comprises a side wall, which bounds an interior of the shield, and a mounting flange, at an end of said side wall, to which said collimator is mountable so as to be supported from the support section via the shield.

Preferably, the shield includes gussets extending between the side wall and flange so as to brace the flange when the collimator is mounted thereto so as to be supported from the support section via the shield.

Preferably, the shield includes a side wall, which bounds an interior of the shield, and a mounting flange, at an end of said side wall, via which said shield is mountable to the support section such that the collimator is supported from the support section via the shield.

The apparatus according to a preferred embodiment of the invention includes a keeper for cabling of the apparatus, the cabling extending from a first component of the apparatus to a second component of the apparatus, one of the components being capable of rotation relative to the other about an axis, the keeper comprising:

a first part fixed to the first component, the first part having a circumferential wall portion which is centred on said axis; and a second part which is fixed to the second component, the second part having a circumferential wall portion which is larger in diameter than the circumferential wall portion of the first part and is centred on said axis, the first and second parts being configured such that they define an annular housing having radially inner and outer walls defined by the circumferential wall portions of the first and second parts respectively, the annular housing holding a section of the cabling extending between the first and second parts in a manner such that a radially outer end of said section is fixed with respect to said radially outer wall and a radially inner end of said section is fixed with respect to said radially inner wall and there is a bend in said section at a position between the ends thereof, the keeper further comprising a guide having circumferential radially outer and inner walls and being configured with a passage which opens through the guide radially outer and inner walls, the guide being configured to occupy the housing so as to be rotatable therein about said axis and such that:

a radially outer channel is defined between the radially outer walls of the housing and guide and holds a portion of said section which is between the radially outer end of the section and the bend ("the radially outer portion"), e.g. in a manner precluding buckling of that portion;

a radially inner channel is defined between the radially inner walls of the housing and guide and holds a part of said section which is between the bend and the radially inner end of the section ("the radially inner portion"), e.g. in a manner precluding buckling of that portion; and said bend extends through said passage, whereby:
rotation of said one component relative to the other component in one rotational direction about the axis urges the bend against the guide to effect rotation of the guide in said one direction in the housing, such that said section moves against the guide, said radially inner portion lengthens and said radially outer portion shortens; and rotation of said one component relative to the other component in the opposite rotational direction about the axis urges the bend against the guide to effect rotation of the guide in said other direction in the housing, such that said section moves against the guide, said radially inner portion shortens and said radially outer portion lengthens.

Preferably, the guide is configured so as to slide relative to said section during the rotation of said one component relative to the other.

Preferably, said passage is configured in the form of a channel complementary in configuration to the bend.

In the keeper in a preferred embodiment, the guide comprises aligned convex and concave surface portions defining side walls of the passage, the convex surface portion being arranged to be abutted by a convex side of the bend such that the urging of the guide in a first one of said rotational directions is effected, and the concave surface portion being arranged to be abutted by a concave side of the bend such that the urging of the guide in a second one of said rotational directions is effected.

Preferably, the keeper is configured such that said axis is substantially upright and said first part comprises a floor portion arranged to support said radially inner portion from below.

Preferably, the keeper is configured such that said axis is substantially upright and said second part comprises a floor portion arranged to support said radially outer portion from below.

Preferably, the first and second parts are configured such that the housing is upwardly opening.

Preferably, the guide is formed separately from the first and second parts so as to be removable from the housing.

Preferably, the first and second parts are separately formed.

The guide is preferably of single-piece construction and is preferably moulded.

Preferably, the first part is of single-piece construction.
Preferably, the first part is moulded.
Preferably, the second part is of single-piece construction.
Preferably, the second part is moulded.
Preferably, the guide is of single-piece construction.
Preferably, the guide is moulded.

Preferably, the first part is configured with an opening arranged such that a section of the cabling extends therethrough, out of the housing, from the radially inner end of the cabling section held by the housing. Preferably, the opening with which the first part is configured passes through the circumferential wall portion of the first part.

Preferably, the second part is configured with an opening arranged such that a section of the cabling extends therethrough, into the housing, to the radially outer end of the cabling section held by the housing.

In a preferred embodiment, a conduit or sheath is arranged over said section of the cabling and configured to permit flexure of said section of the cabling during the rotation of said one component relative to the other.

The conduit or sheath may be configured to flex with the cabling. The conduit or sheath so configured may comprise flexible tubing.

The conduit or sheath may be articulated about axes which are parallel to the axis of rotation, so as to permit said flexure of the cabling. The articulated conduit or sheath may comprise chain conduit.

Preferably, the radially inner end of the cabling section is anchored to the first component and/or the radially outer end of the cabling section is anchored to the second component.

In a preferred embodiment, the conduit or sheath is:
to effect the anchorage of the radially inner end of the cabling section to the first part, connected to the first component at a position adjacent that end; and/or
to effect the anchorage of the radially outer end of the cabling section to the second part, connected to the first component at a position adjacent that end.

In a preferred embodiment, the cabling is configured in the form of a strip the opposed faces of which align with said axis.

Preferably, the one component comprises a collimator and/or backscatter shield of the apparatus and the other component includes radiation source of the apparatus.

Preferably, one component includes said arm and a radiation source of said head, and the other component includes a body section of the apparatus to which a proximal end of the arm is connected in a manner such that the arm can slew relative to the body section about the axis of rotation.

The content of Australian provisional patent application no. 2015904310, filed 21 Oct. 2015, is incorporated herein by reference.

BRIEF DESCRIPTION OF THE DRAWINGS

The invention will now be described, by way of non-limiting example only, with reference to the accompanying drawings, in which.

DETAILED DESCRIPTION OF THE PREFERRED EMBODIMENT(S) OF THE INVENTION

Figure 1:
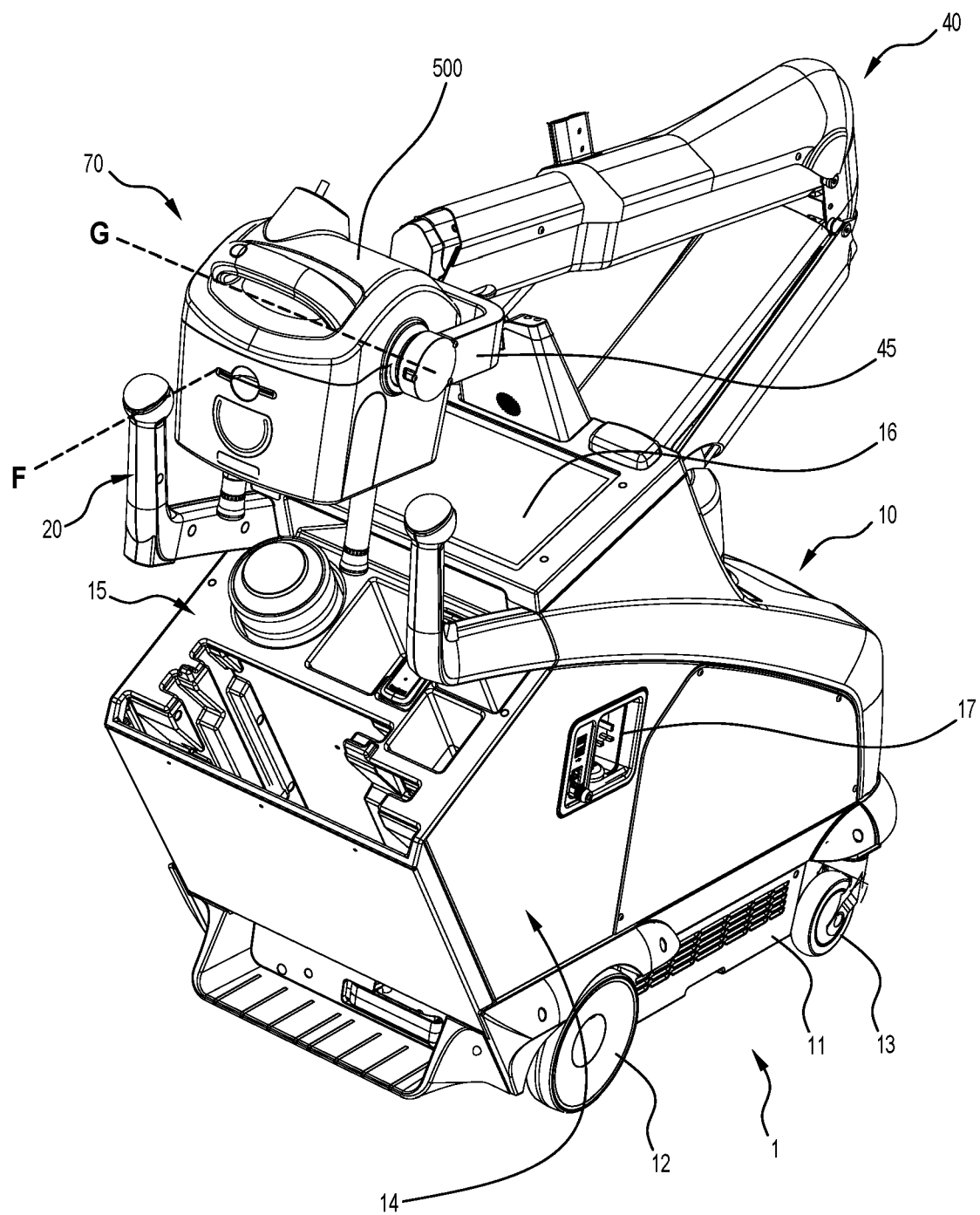
FIG. 1 is a rear perspective view of an X-ray cart in accordance with a preferred embodiment of the present invention.
Figure 2:
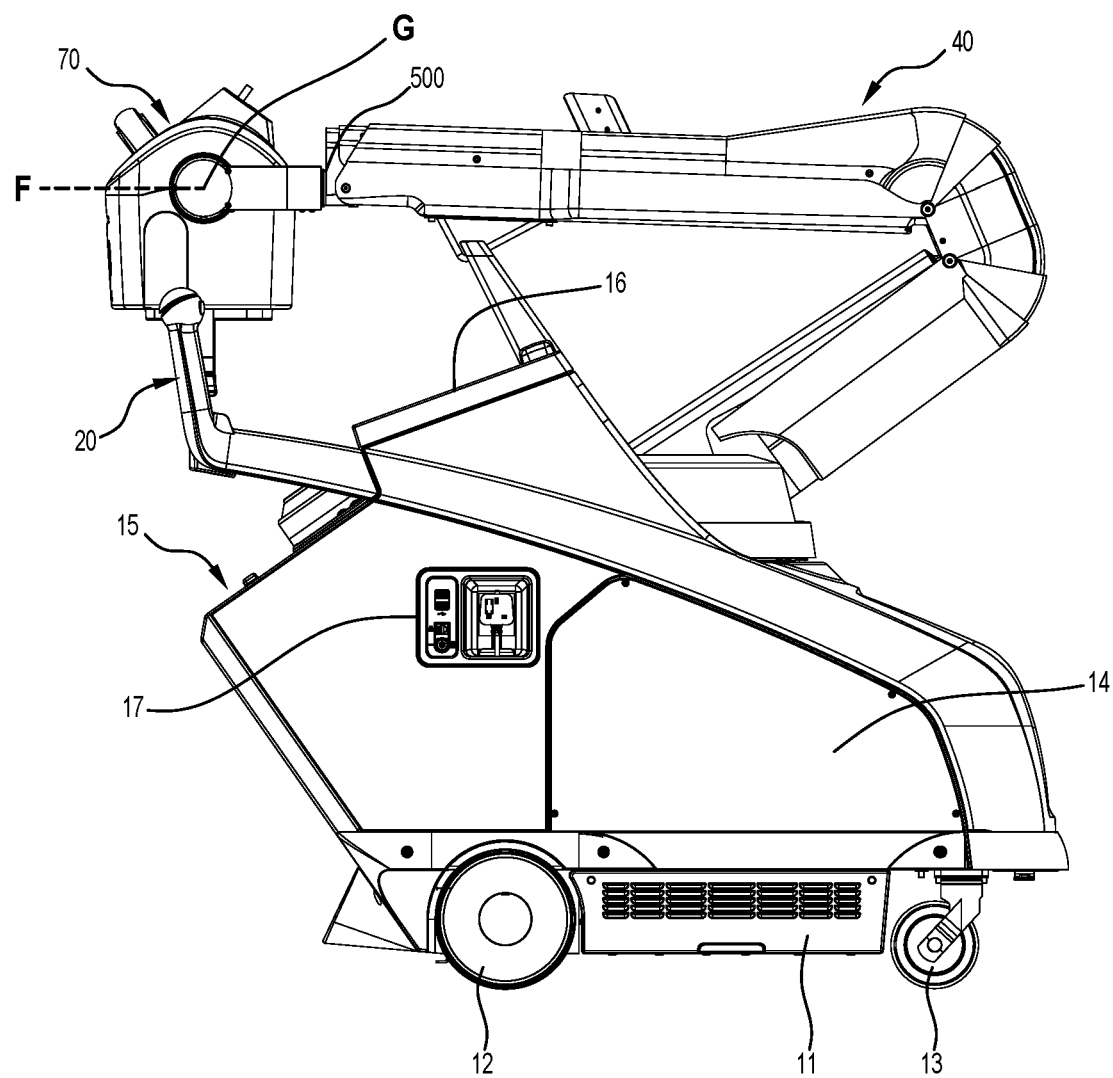
FIG. 2 is a side elevation view of the cart.

Shown in FIGS. 1 and 2 is an X-ray cart 1 according to a preferred embodiment of the present invention. The cart 1 comprises a main body 10, an articulated arm 40, connected at a proximal end thereof to the body 10 so as to be supported by the body 10, and an X-ray tube head 70 which is supported from a distal end of the arm 40 via a yoke 45.

Figure 37:
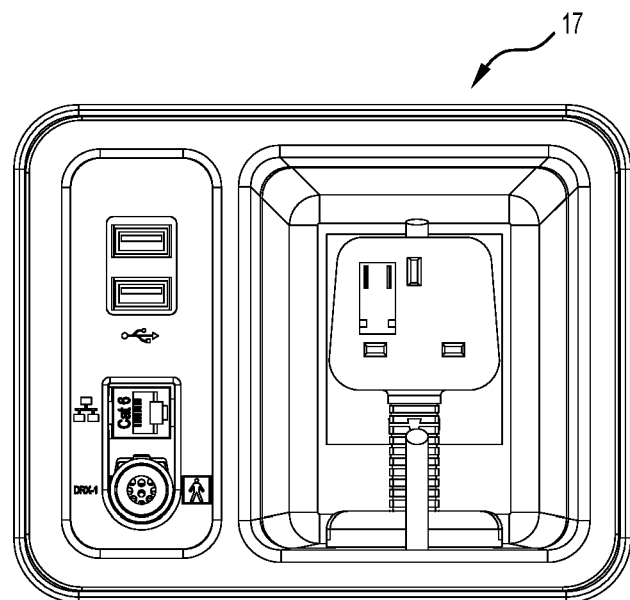
FIG. 37 shows details of an electrical/data transfer/power connection console of the cart.

The main body 10 includes a chassis 11 and ground-engaging wheels, on which the chassis 11 is supported, the wheels comprising coaxial rear wheels 12, the rotational axis of which is fixed relative to the chassis 11, and front wheels 13 defined by castors. The main body 10 further includes a housing 14, a control console 15 arranged at a rear position on the housing 14, a rearwardly and upwardly facing output display 16 (which, inter alia, displays an X-ray image which has been taken by the cart 1), arranged adjacent and forwardly of the console, and a recharging/data transfer/electrical connection point 17, shown in further detail at FIG. 37, to which a charging cable can be connected for the purposes of charging an on-board power supply of the cart 1.

Figure 3:
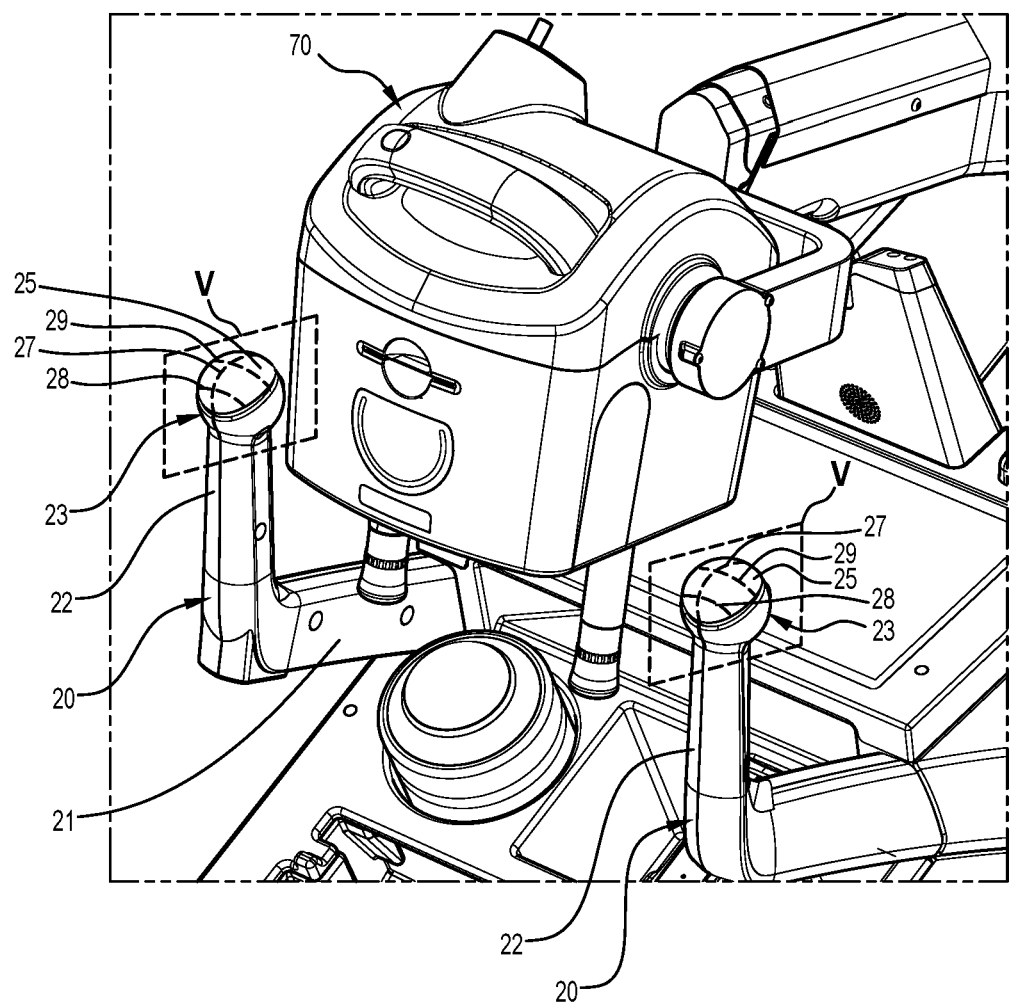
FIG. 3 is a rear perspective view showing a handle arrangement of the cart, which arrangement is operable manoeuvre the cart.
Figure 4:
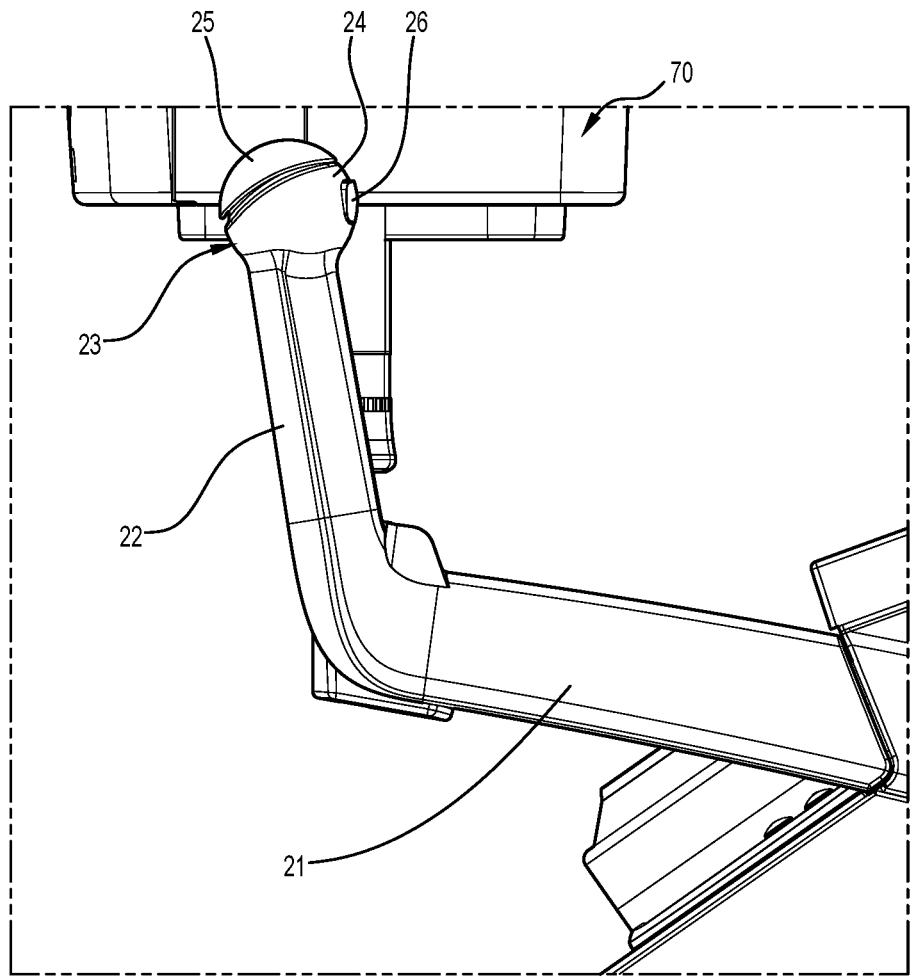
FIG. 4 is a side view showing a right-hand handle of the handle arrangement.
Figure 5:
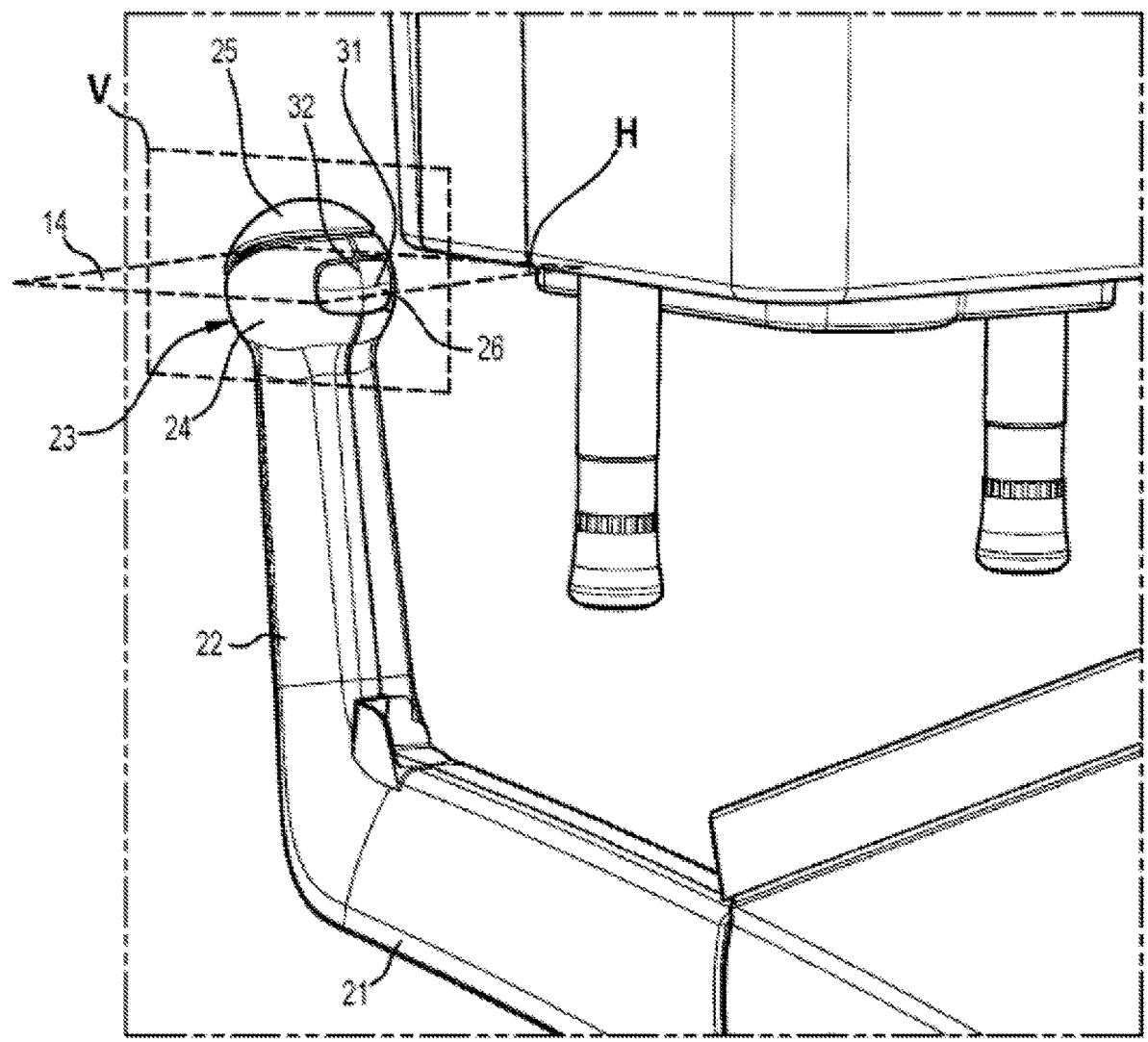
FIG. 5 is a front perspective view of the handle.
Figure 6:
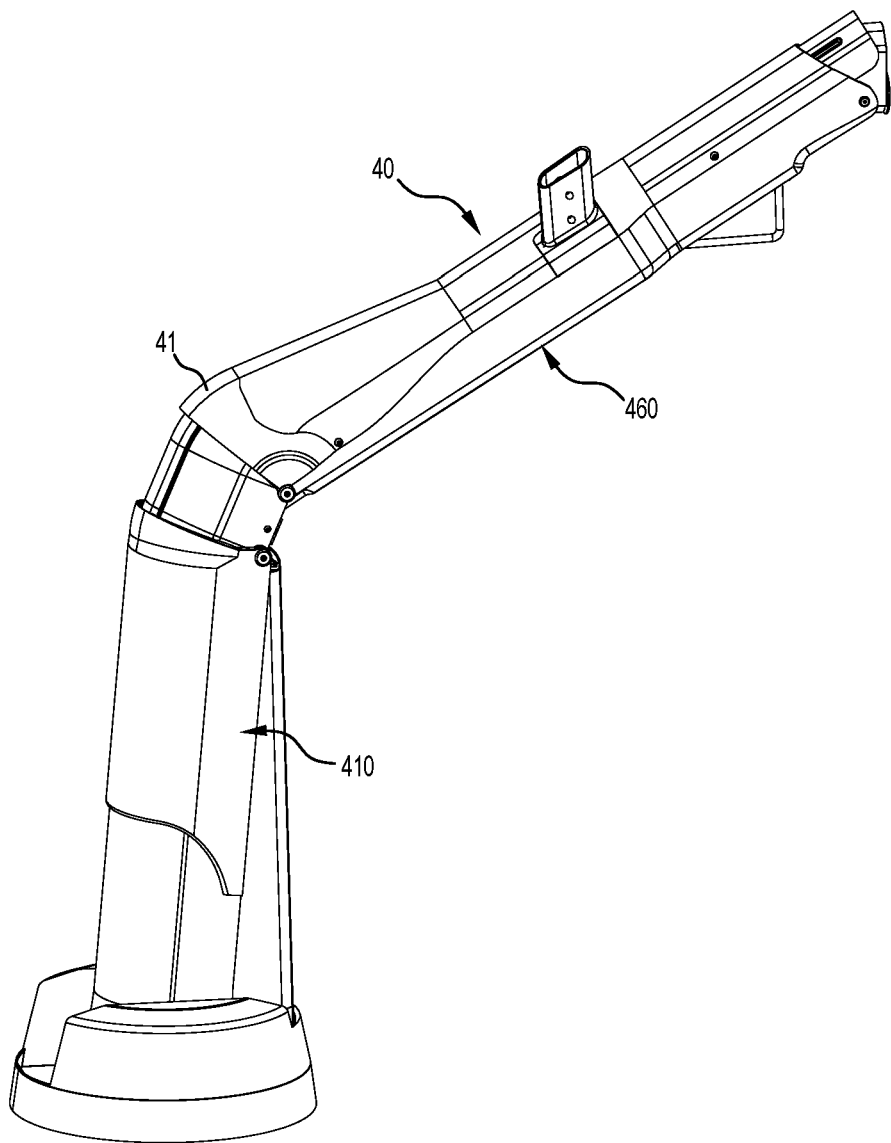
FIG. 6 is a perspective view of an articulated arm assembly of the cart.

The cart 1 further includes, referring to FIGS. 3 to 5, a pair of spaced apart, side-by-side, handle members 20, each of which is arranged at a rear position of the cart 1 on a respective lateral side of the cart 1. Each member 20 is configured with a first section 21, which projects rearwardly from the body 10, and a second section 22, which projects generally upwardly from a rear end of the first section 21, the handle member thus having a generally L-shaped configuration.

Each handle member 20 includes, arranged at an upper end of the second section 22 thereof, a respective bulbous or ball-shaped grip 23 which a person can grasp with a respective one of his or her hands in order to manoeuvre the cart 1 over a floor surface on which it is supported. An exterior of each grip 23 is defined by a fixed portion 24, a palm actuator 25, at a generally rearward position in the grip 23, and a finger actuator 26, at a generally forward position in the grip 23. Each of the actuators 25 and 26 is, in the present embodiment, a button, and is arranged such that, when depressed, it releases electrically controlled, e.g. solenoid, brakes of the cart 1, permitting pushing or pulling of the cart 1 along a floor surface on which the cart 1 is supported. More particularly, the actuators 25 and 26 form part of a braking system of the cart 1 which is electrically coupled to the power supply and configured such that, when any one of those four actuators is depressed, current from the DC power supply flows to one or more solenoids which thus operate to release brakes engaging the rear wheels 12, by overcoming a resilient bias which maintains the brakes in engagement with the wheels 12 when current is not supplied to the solenoid(s), the brakes being thus "fail-safe". Brakes of this kind are well known in the art. The actuator buttons 25, 26 of each grip 23 are arranged such that, when a person, standing at the rear of the cart 1 and facing forwardly, grasps that grip from above, the palm of the hand grasping it is received against the button 25 and fingers of that hand are received against the button 26. Application of palm and finger pressure to the buttons 25 and 26 respectively, e.g. by squeezing of the grip between palm and fingers, causes the buttons 25 and 26 to be depressed, such that the brakes are released.

Referring to FIGS. 3 and 5, in each grip 23, the two actuators 25 and 26 are centrally and symmetrically disposed about a respective vertical plane V which is substantially orthogonal to the axis of rotation of the wheels 12. The (main) surface of the actuator 25 extends in a longitudinal arc 27 which is arranged in the plane V, a proximal transverse arc 28, and a distal transverse arc 29, the arcs 27, 28 and 29 being arranged such that, when the respective grip is grasped in the manner described above, longitudinal arc, proximal arc and distal arc, respectively, of the grasping hand. The proximal/rear and distal/forward ends of each button 25 are curved such that the surface of the button 25 assumes a substantially elliptical, outwardly convex configuration. Referring to FIG. 5, the button 26 of each grip 23 is symmetrical and centred about a horizontal plane H which, like the plane V, passes through the geometric centre of the ball shape of the grip. The surface of the button 26 extends through a transverse/horizontal arc 31, lying in the plane H, and extends in an arc 32 lying in the plane V.

The grips are positioned such that, assuming the person is an adult of average height, his or her forearms will be generally parallel and horizontal when he or she, while standing upright, grasps the grips with respective hands and when that person's upper arms are substantially vertical and adjacent respective lateral sides of his or her torso. Advantageously, owing to the positioning and configuration of the buttons 25, 26, application of palm pressure to either grip 23 through the hand engaging it (even if none of the fingers of that hand are urged against the button 26) will inevitably cause depression of the button 25, effecting release of the brakes such that the so-applied palm pressure causes the cart 1 to be pushed over the floor, and application of finger pressure to either grip 23 by the hand engaging it will (irrespective of whether the palm of that hand is urged against the actuator button 25 on that grip) cause the button 26 to be depressed, such that the brakes are disengaged and the so-applied finger pressure pulls the cart 1 over the floor.

Each of the buttons 25 and 26 is arranged such that, in its extended (unengaged) condition, it projects proud of the fixed section 24, i.e. the surface thereof is radially outward of the surface of an imaginary sphere in which the exterior face of the fixed section 24 lies. Each of the buttons 25 and 26 has a stroke which is such that, when it is fully depressed, the surface thereof is substantially flush with the surface of the fixed section 24, i.e. at the face of the imaginary sphere.

The cart 1 may, without departure from the invention, be modified such that the height at which each of the grips 23 is positioned can be adjusted and/or such that the transverse spacing of the grips 23 can be adjusted and/or such that the angular orientation of the grips 23 can be adjusted.

Also, the actuators may, without departure from the invention, be manually engagable in a different manner. For example, they may be touch-activateable (rather than being defined by depressible buttons). To this end, the actuators may, for example, be defined by capacitive sensors which are activateable by being touched by a person's skin.

It is also possible, without departure from the invention, for only one of the two grips 23 to be configured with the actuator buttons 25, 26 (the other grip, for example, having an exterior which is substantially fixed throughout) whereby disabling of the brakes relies on the person engaging that particular grip.

Additionally, without departure from the invention, the grips 23 may assume a different orientation; for example, they may be arranged such that each projects laterally outwardly (rather than upwardly) from the upper end of the respective section 22, whereby the person's hands assume a "palms-in" orientation when grasping the respective grips. In that instance, the plane about which the actuators 25 and 26 are centred would be horizontal, instead of being vertical and parallel to the longitudinal axis of the cart 1.

Furthermore, without departure from the invention, on each grip 23, either of the buttons 25 and 26 may constitute the only actuator button, though generally it will be far preferable that both buttons be present.

Referring to FIGS. 12 to 22, the X-ray tube head 70 includes, consistent with conventional X-ray heads, an X-ray source 71 (see FIG. 13), which includes an X-ray tube 72, and, rotatable relative to the source 71, an assembly comprising a backscatter shield 80 (see FIG. 14) and a collimator 90 ("the shield/collimator assembly"). The X-ray head 70 further comprises a keeper 200, interposed between the source 71 and the shield/collimator assembly, which houses and guides an electrical cable 201 of the cart, which cable takes the form of a strip, as will be described in further detail later.

Figure 17:
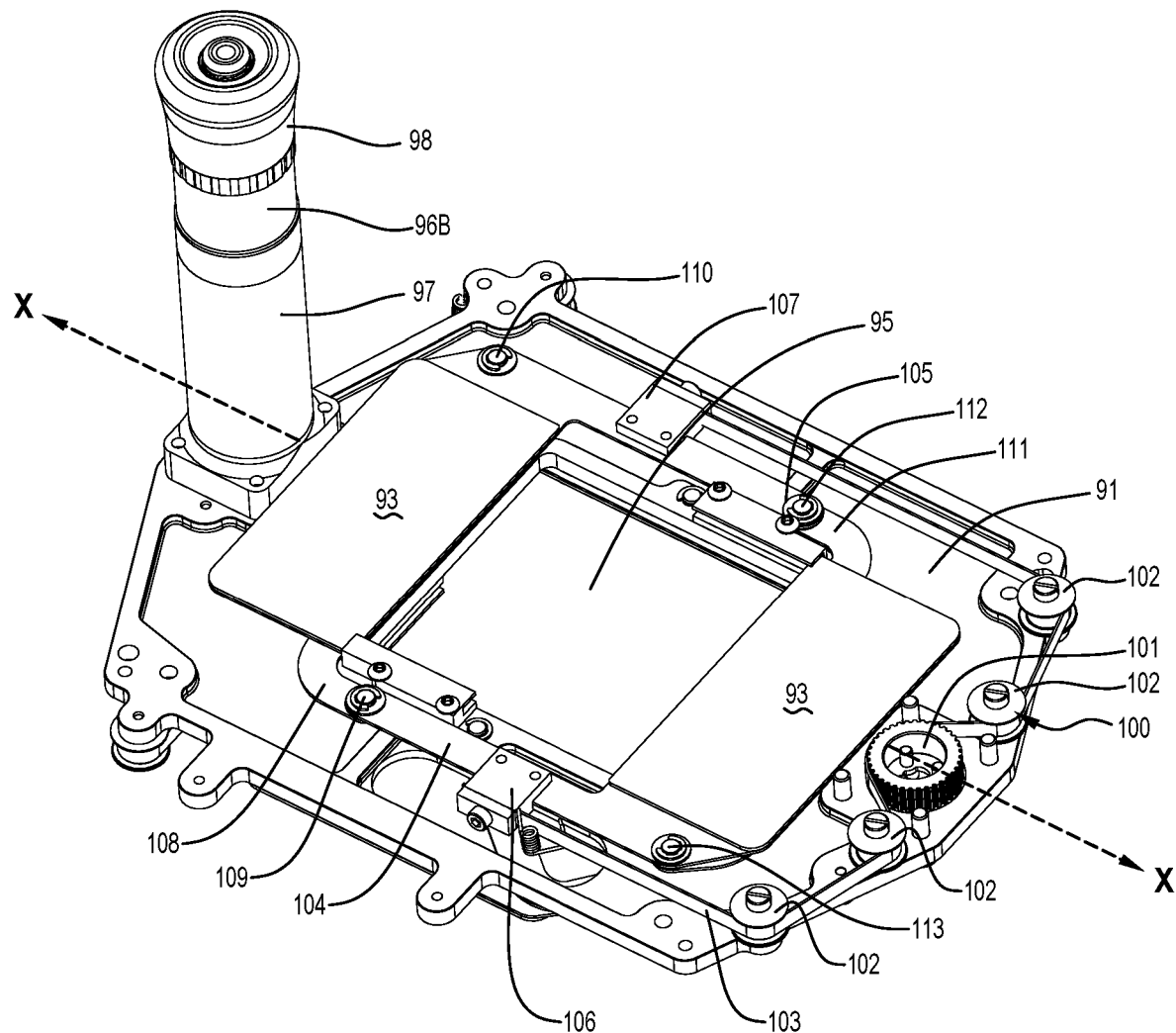
FIG. 17 is a perspective view showing details of the collimator from below.
Figure 18:
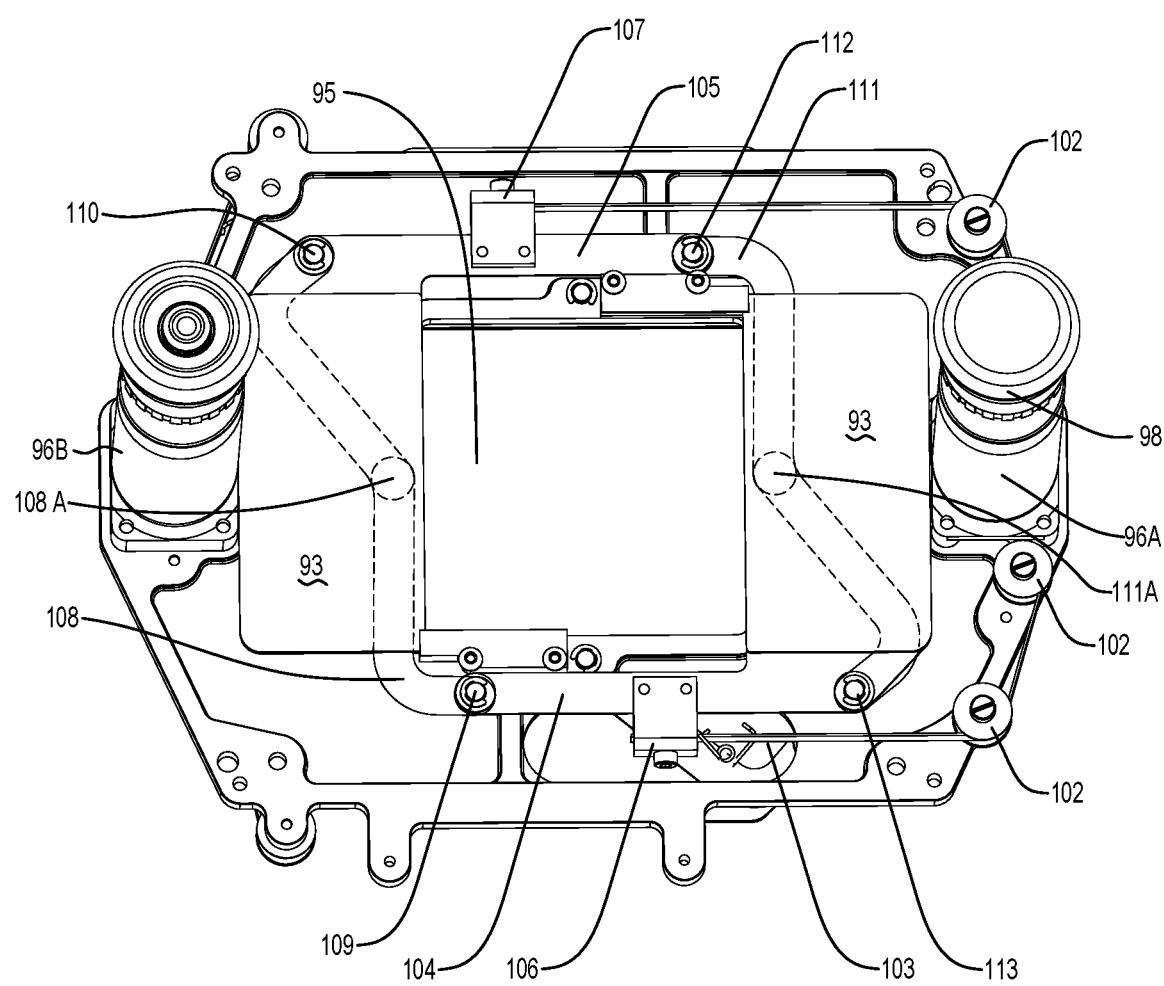
FIG. 18 is a perspective view corresponding to that shown in FIG. 17 but indicating configurations of connecting rods or arms of the collimator.
Figure 19:
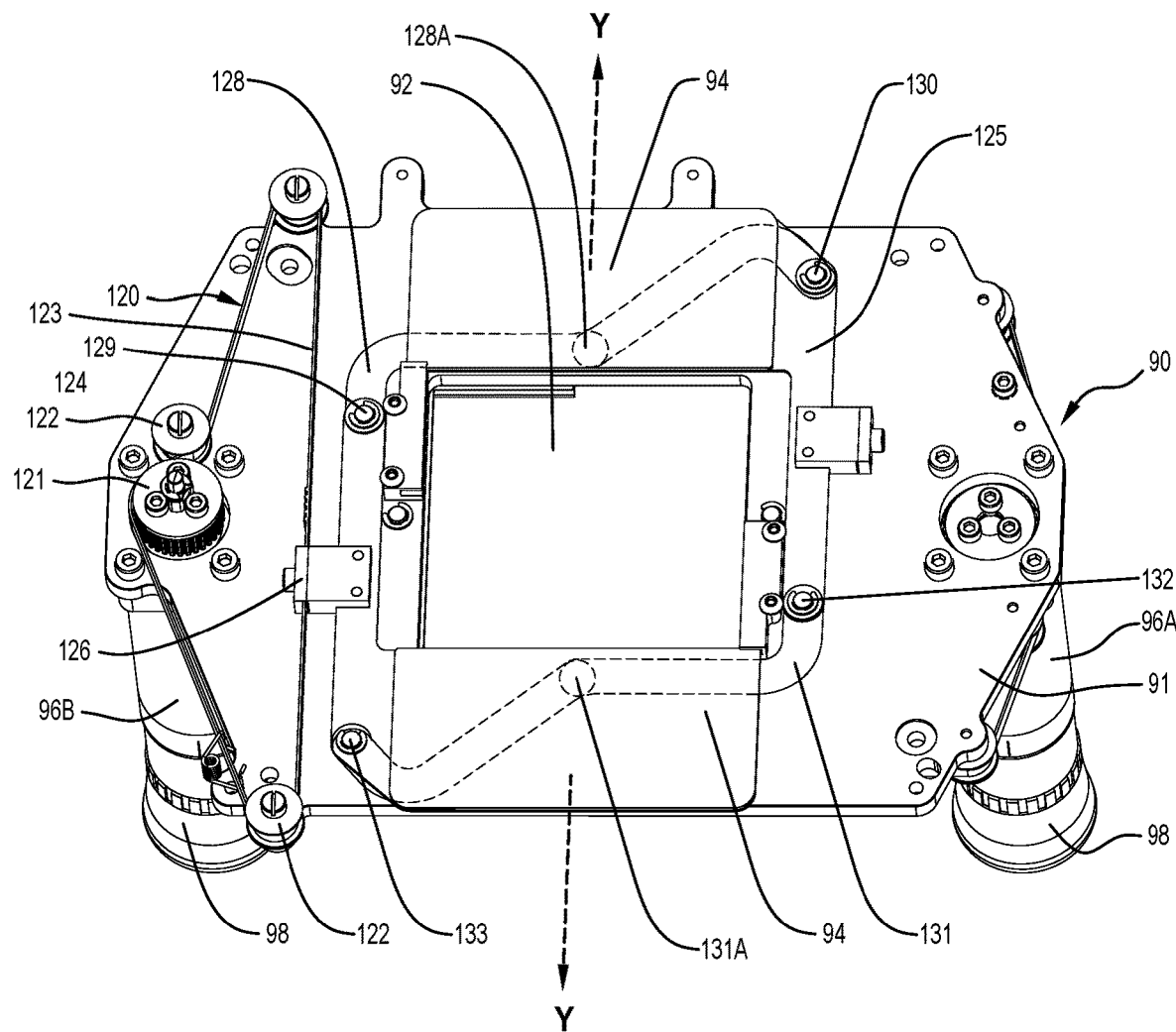
FIG. 19 is a perspective view showing details of the collimator from above and indicating configurations of other connecting rods or arms of the collimator.
Figure 20:
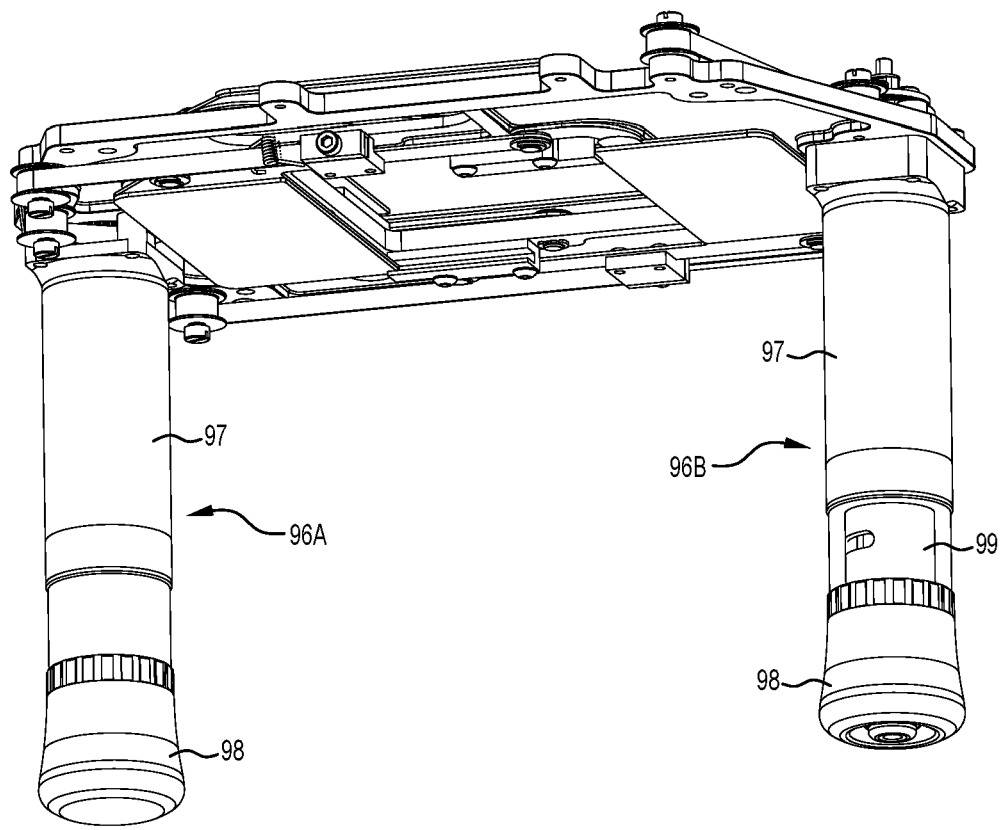
FIG. 20 is a side perspective view showing details of the collimator, including tusks for adjusting translational and rotational positions of the X-ray head, as well as the dimensions and rotational orientation of an aperture of the collimator.

Referring to FIGS. 17 to 19 in particular, the collimator 90, consistent with conventional collimators, comprises an X-ray-reflective base plate 91, configured with an opening 92 therethrough, a first pair of X-ray-reflective shutters 93, arranged on an underside of the base plate and movable, towards or away from each other, along a first axis X, and a second pair of X-ray-reflective shutter plates 94, arranged on the top side of the base plate 91 and movable, towards or away from each other, along a second axis Y, the Y axis being perpendicular to the X axis. Accordingly, the length and width dimensions of an aperture 95, defined by the area of the opening 92 uncovered by the plates 93 and 94, is adjustable. The collimator 90 comprises laterally opposed projections, in the form of tusks 96A and 96B, which are connected to and project downwardly from the base plate 91. The tusks can be grasped such that the position of the head 70 can be adjusted (including by articulating and/or slewing the arm 40 as/where necessary). Referring also to FIG. 20, each tusk is configured with a generally cylindrical fixed section 97, an upper end of which is secured to the base plate 91, and a generally cylindrical rotatable knob 98, arranged at a lower end of the fixed section 97 and rotatable relative to that section. Each tusk further includes an internal shaft 99 (see in FIG. 20, in which detail of some of the exterior of tusk 96B is omitted such that the shaft 99 is shown), which passes through the fixed section 97 and is engaged, at a lower end thereof, by the respective knob 98 (in any suitable manner as will be known to a person skilled in the art). The shaft 99 is secured at its upper end to a pulley of a respective adjustment mechanism for effecting the movement of the pairs of shutter plates 93 and 94, whereby rotation of the rotatable section 98 drives the pulley to effect the movement of the respective plates. The adjustment mechanism will now be described.

FIGS. 17 and 18 show the mechanism 100 for adjustment of the plates 93, the mechanism 100 comprising a toothed pulley 101, as previously mentioned, rollers 102 and a toothed belt 103 which is trained over the pulley 101 and rollers 102. The mechanism 100 includes a first arm 104 attached to one of the plates 93 and a second arm 105 which is parallel with and opposed to the first arm 104, and is connected to the other plate 93. The mechanism 100 additionally includes a connector 106 which connects one end of the belt 103 to the arm 104, and a connector 107 which connects the other end of the belt 103 to the arm 105. The mechanism 100 further comprises a third arm 108 which is pivotally connected at one end thereof, via pivot 109, to a distal end of the arm 104 and extends, between a first one of the plates 93, shown on the left in FIGS. 17 and 18, and the base plate 91, to the proximal end of the arm 105, to which end the arm 108 is pivotally connected, via a pivot 110, at its other end. The arm 108 is, at a position between the pivots 109 and 110, pivotally connected with the base plate 91, via a pivot 108A. The mechanism 100 further comprises a fourth arm 111 which is pivotally connected at one end thereof, via pivot 112, to a distal end of the arm 105 and extends, between the second plate 93, shown on the right in FIGS. 17 and 18, and the base plate 91, to the proximal end of the arm 104, to which end the arm 111 is pivotally connected, via a pivot 113, at its other end. The arm 111 is, at a position between the pivots 112 and 113, pivotally connected with the base plate 91, via a pivot 111A.

FIG. 19 shows the mechanism 120 for adjustment of the plates 94, the mechanism 120 comprising a toothed pulley 121, as previously mentioned, rollers 122 and a toothed belt 123 which is trained over the pulley 121 and rollers 122. The mechanism 120 includes a first arm 124 attached to one of the plates 94 and a second arm 125 which is parallel with and opposed to the first arm 124, and is connected to the other plate 94. The mechanism 120 additionally includes a connector 126 which connects both ends of the belt 123 to the arm 124. The mechanism 120 further comprises a third arm 128 which is pivotally connected at one end thereof, via pivot 129, to a distal end of the arm 124 and extends, between a first one of the plates 94, shown in the background part of FIG. 19, and the base plate 91, to the proximal end of the arm 125, to which end the arm 128 is pivotally connected, via a pivot 130, at its other end. The arm 128 is, at a position between the pivots 129 and 130, pivotally connected with the base plate 91, via a pivot 128A. The mechanism 120 further comprises a fourth arm 131 which is pivotally connected at one end thereof, via pivot 132, to a distal end of the arm 125 and extends, between the second plate 94, shown in the foreground part of FIG. 19, and the base plate 91, to the proximal end of the arm 124, to which end the arm 131 is pivotally connected, via a pivot 133, at its other end. The arm 131 is, at a position between the pivots 132 and 133, pivotally connected with the base plate 91, via a pivot 131A.

Figure 16:
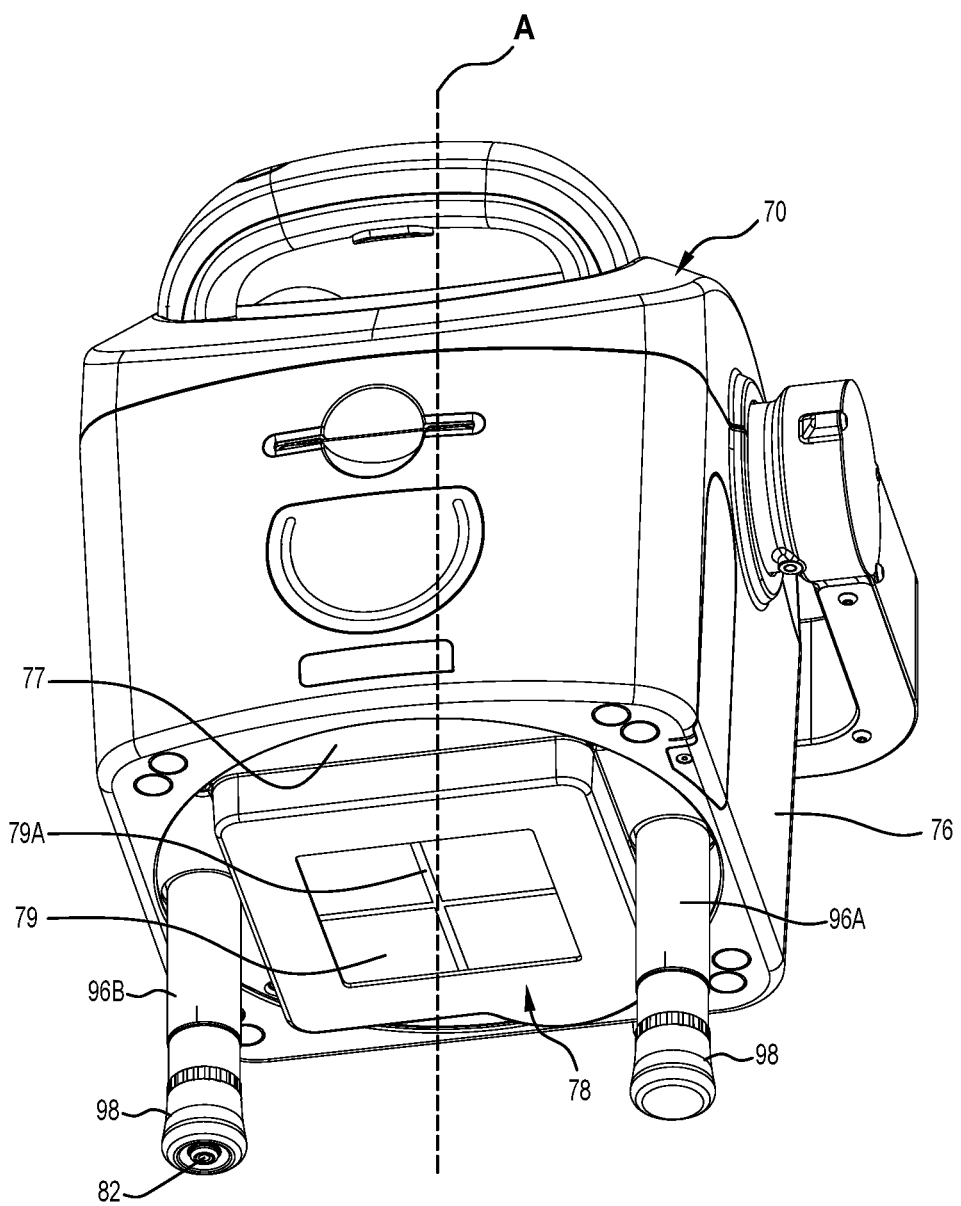
FIG. 16 is a lower perspective view of the tube head showing, inter alia, external features of the collimator.

Referring to FIG. 16, the X-ray head 70 includes a casing structure 76 which is configured with a downwardly facing opening 77. The shield/collimator assembly includes a circular cover 78, through which top ends of the tusks 96A, 96B extend, that is secured to the underside of the base plate 91, the cover 78 being rotatable, with the rest of the shield/collimator assembly, about an axis A, shown in FIG. 16, relative to the casing structure 76. The cover 78 shields the mechanism 100 and includes or holds a window 79 which is configured with crosshairs 79A. The cover 78 and casing structure 76 define a housing of a main body section of the head. The shield/collimator assembly, referring to FIG. 14, includes a light source 81 arranged to emit light, through a light-admitting hole (not shown) in a side wall of the shield 80, such that the light is incident on a mirror (also not shown) which is transmissive/transparent to a beam of X-rays from the X-ray source 71 arranged within the shield 80 and on the axis A, at 45 degrees to a plane normal to that axis, such that light from the light source 81 is directed, through the aperture 95 and thence the window 79 whereby a projection of the aperture and crosshairs will be formed on a patient/subject, over the body part of the patient/subject to be X-rayed. Arranged at a lower end of the tusk 96B, more particularly at the underside of the adjustor 98 thereof, is a switch 82, which in the present embodiment takes the form of a button, for switching the light source 81 on and off.

Figure 13:
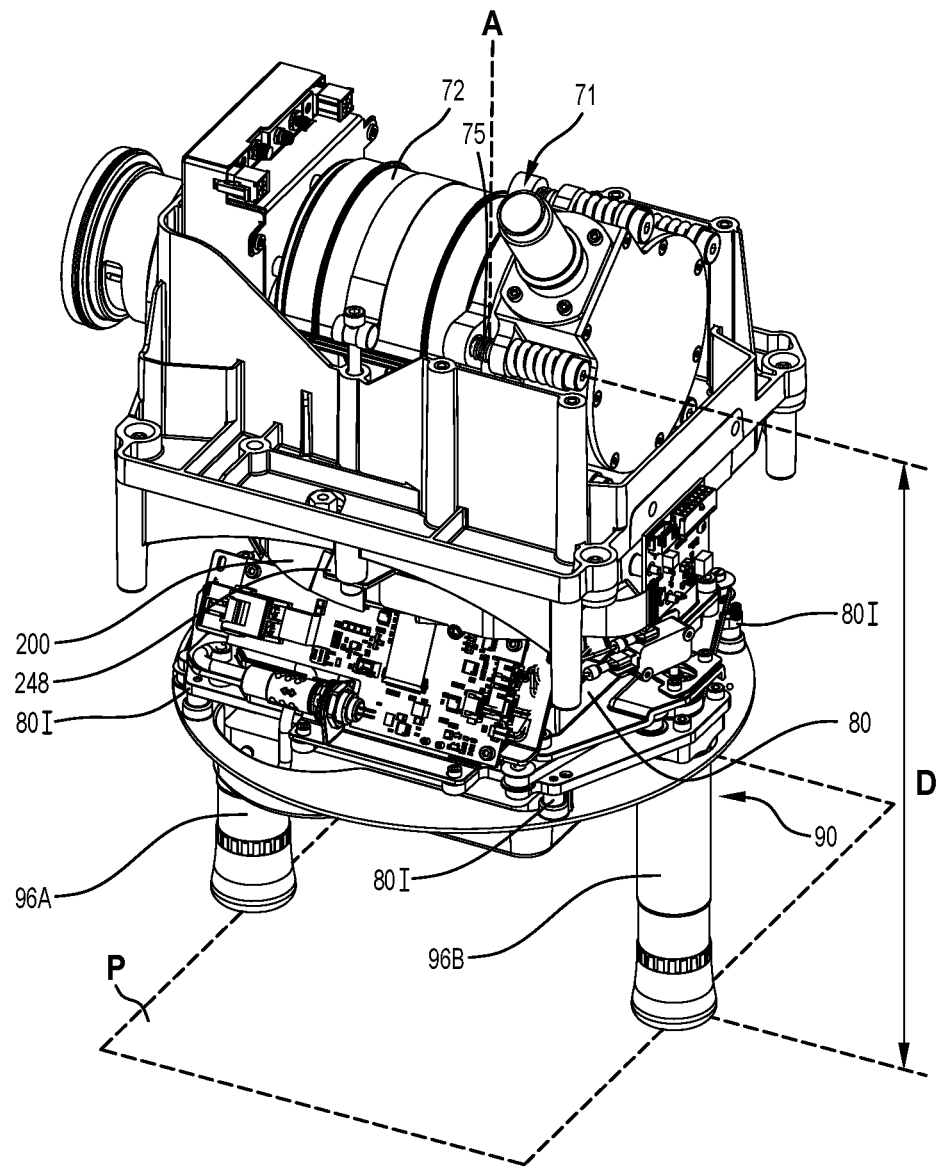
FIG. 13 is a rear perspective view showing details of an X-ray source and collimator of the X-ray head (with a casing of the head removed)
Figure 14:
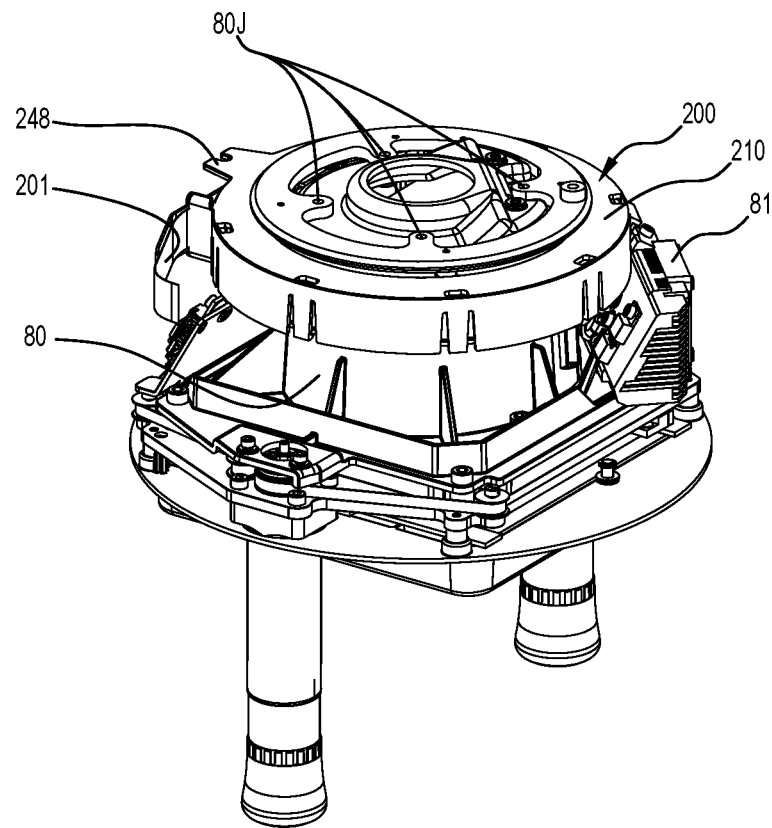
FIG. 14 is an upper perspective view showing details of the collimator, a backscatter shield and an electrical cable keeper, all of which form part of the tube head.
Figure 15:
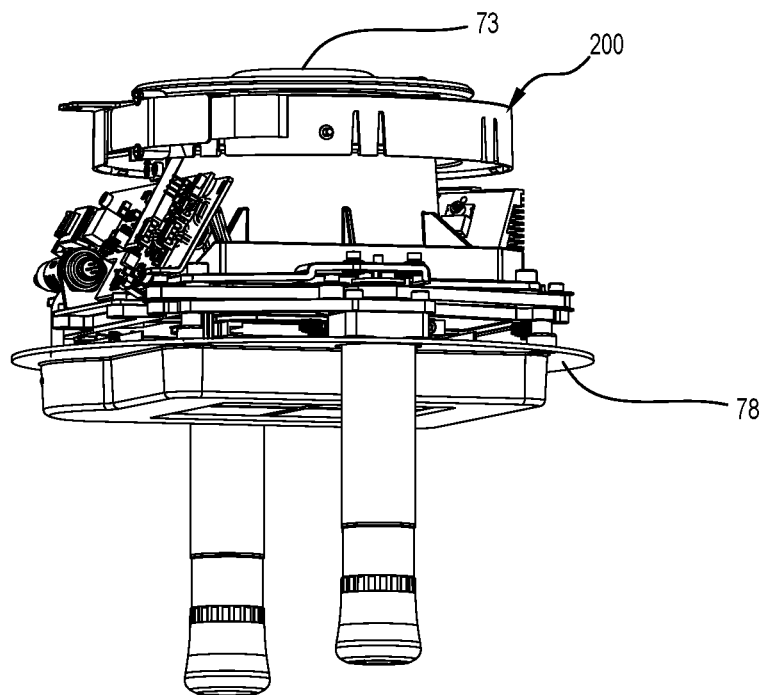
FIG. 15 is a side perspective view of the arrangement shown in FIG. 14.

The X-ray head 70 is, consistent with conventional X-ray heads, configured such that an X-ray beam from the X-ray tube/source has a focal spot, the position of which, shown with reference numeral 75 in FIG. 13, lies on the axis A. Generally speaking, safety requirements are such that the distance between the focal spot and a subject/patient, typically called the "focal spot-to-skin distance", must not be less than a particular minimum value. The X-ray head 70 is configured such that the lowermost extents/tips of the tusks 96A and 96B lie in a plane P which is positioned at a perpendicular distance D from the focal spot 75, which distance is equal to, or only very slightly greater than, the aforementioned minimum value, which is typically 30 cm. Advantageously, the tusks 96A and 96B thus define a gauge for ensuring that the X-ray head 70 is not positioned too close to the subject/patient; more specifically, when the head 70 is orientated adjacent the subject/patient, over the body part to be X-rayed, the operator, by ensuring that no part of the patient/subject's body, which the window 79 faces, passes through the plane P, ensures that the distance between the focal spot 75 and the patient/subject's body is greater than the minimum allowable spacing. The operator can use the tusks 96A and 96B either as a visual gauge, judging by eye that the body part being X-rayed does not protrude through the plane P in the direction towards the focal spot 75 and/or can bring the tip of either or each of the tusks 96A and 96B into contact with the subject/patient, such that there is defined a stopper, comprising the tusk(s) contacting the subject/patient, precluding the head 70, and thus the focal spot 75, from being positioned any closer to the subject/patient.

Advantageously, owing to the collimator adjustors 98 being arranged on tusks 96A and 96B, especially at lower ends of the tusks, which project downwardly, away from the casing structure 76, the X-ray head 70 can be arranged higher above the subject/patient with the controls 98, 82 remaining within the operator's reach. The operator can thus position the focal spot 75 further from the subject/patient, while maintaining his or her ability to operate the controls, 98, 82, than if those controls were on or adjacent to the housing 76, whereby the subject/patient's radiation exposure, resulting from the taking of the X-ray with the focal spot so positioned, is reduced. Conveniently, the operator, after locating the X-ray head 70 in the appropriate position to take a given X-ray and/or rotating the shield/collimator assembly about the axis A, by grasping and manipulating the tusks 96A, 96B (such that the window 79 is appropriately located for the purposes of taking an X-ray of the patient/subject), can activate the light, by hand-operating the switch 82, and/or adjust the aperture size, by hand-operating either or each of the adjustors 98, to establish the appropriate projection on the subject/patient, the projection illuminating the frame of the X-ray image that will be taken (with the intersection of the projection of the crosshairs 79A pin-pointing the centre of that frame).

Figure 21:
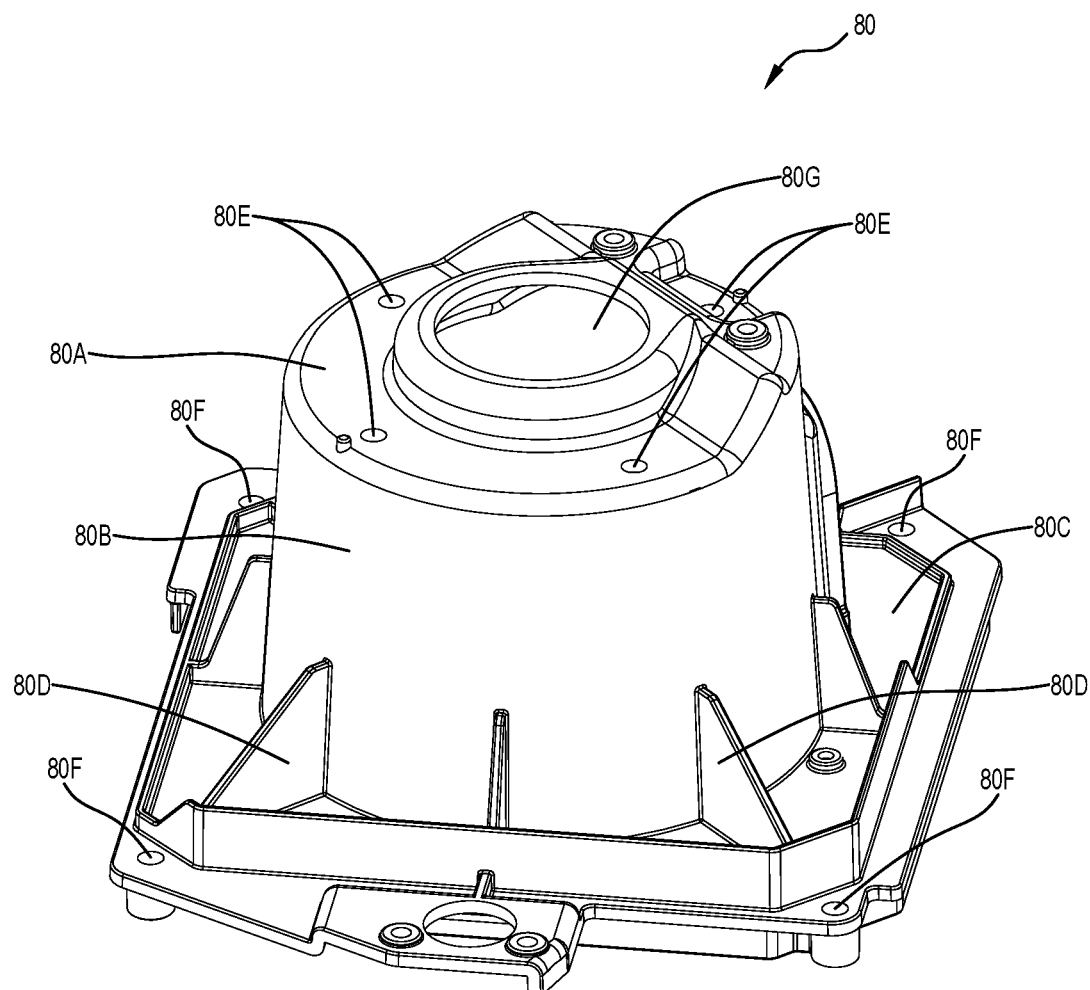
FIG. 21 is a perspective view of the backscatter shield from above.
Figure 22:
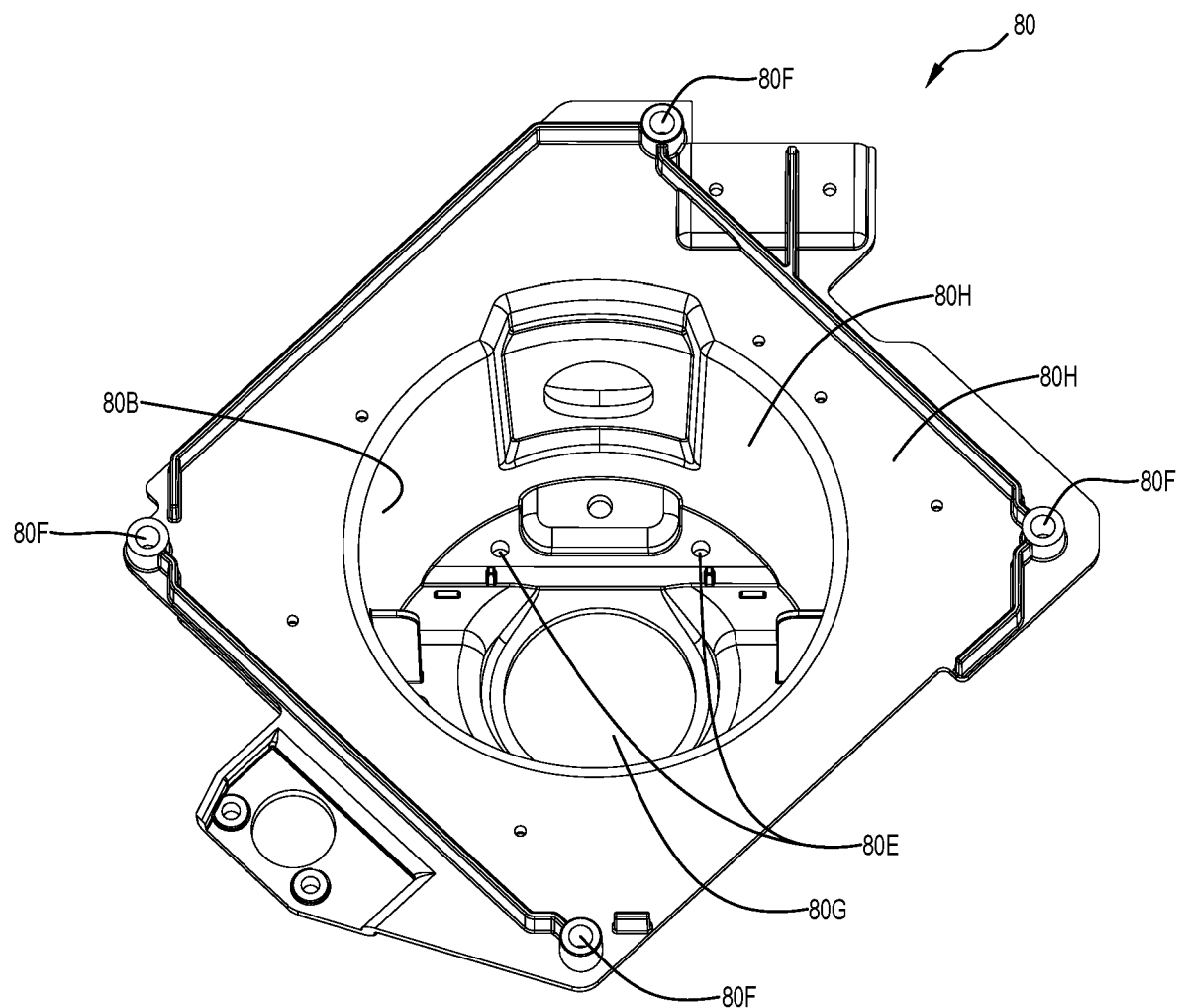
FIG. 22 is a perspective view of the backscatter shield from below.

The backscatter shield 80, shown in further detail at FIGS. 21 and 22, comprises a roof section 80A, a downwardly divergent, generally frustoconical, side wall section 80B, configured with the aforementioned light-admitting hole (not shown), which section extends from the roof section 80A, and a base section 80C, comprising a flange, at the lower end of the sidewall 80B. The shield 80 further includes gussets 80D arranged at spaced positions around the sidewall 80B, each gusset 80D extending between the base 80C and sidewall 80B. The backscatter shield 80 is configured with mounting holes 80E, formed through the roof section 80A, and mounting holes 80F, formed through the base 80C, at corners thereof. The shield 80 further includes a central opening 80G through the roof section 80A, through which opening an X-ray beam projects from the X-ray source 71 when in operation, and an opening 80H through the base 80C, through which opening the beam passes such that radiation passes through the aperture 95 and thence to the subject/patient. Referring also to FIG. 13, threaded fasteners 801 are received through respective holes in the base plate 91 and the holes 80F in the shield base 80C, whereby the former is mounted to the latter, such that the collimator assembly hangs or depends from the shield 80. The shield 80 thus supports the weight of the collimator assembly 90, loads exerted on the shield 80 as a result of that weight being transferred, from the shield base 80C to the shield side wall 80B through gussets 80D. The shield roof section 80A is, referring to FIG. 14, secured to a central, rotatable, part of the keeper 200 via threaded fasteners 80J which are passed though respective ones of the mounting holes 80E. The collimator assembly 90 is thus suspended from the keeper 200 via the shield 80, the shield 80 thus, in addition to serving its conventional role of absorbing X-ray radiation reflected by the base plate 91, and shutter plates 93 and 94 and their surroundings, forming a structural or supportive component in the shield/collimator assembly and in the X-ray head 70.

The shield 80 is moulded, preferably by injection moulding, as a single piece from a composite comprising tungsten powder and a polymeric binder, such as nylon $12^R$. A suitable such material is that which is supplied by Ecomass Technologies LP, based in Austin, Tex., under the trade name Ecomass, and is disclosed in detail in the specification and drawings of Australian patent no. 741567, the entire content of which is incorporated herein by reference. Advantageously, the shield 80 is much lighter than it would be if formed from lead, whereby the weight of the cart 1 is, in turn, reduced, as is a given moment, exerted about the chassis as a result of the articulated arm 40 and X-ray head 70 being cantilevered from the body 10 of the cart.

Figure 23:
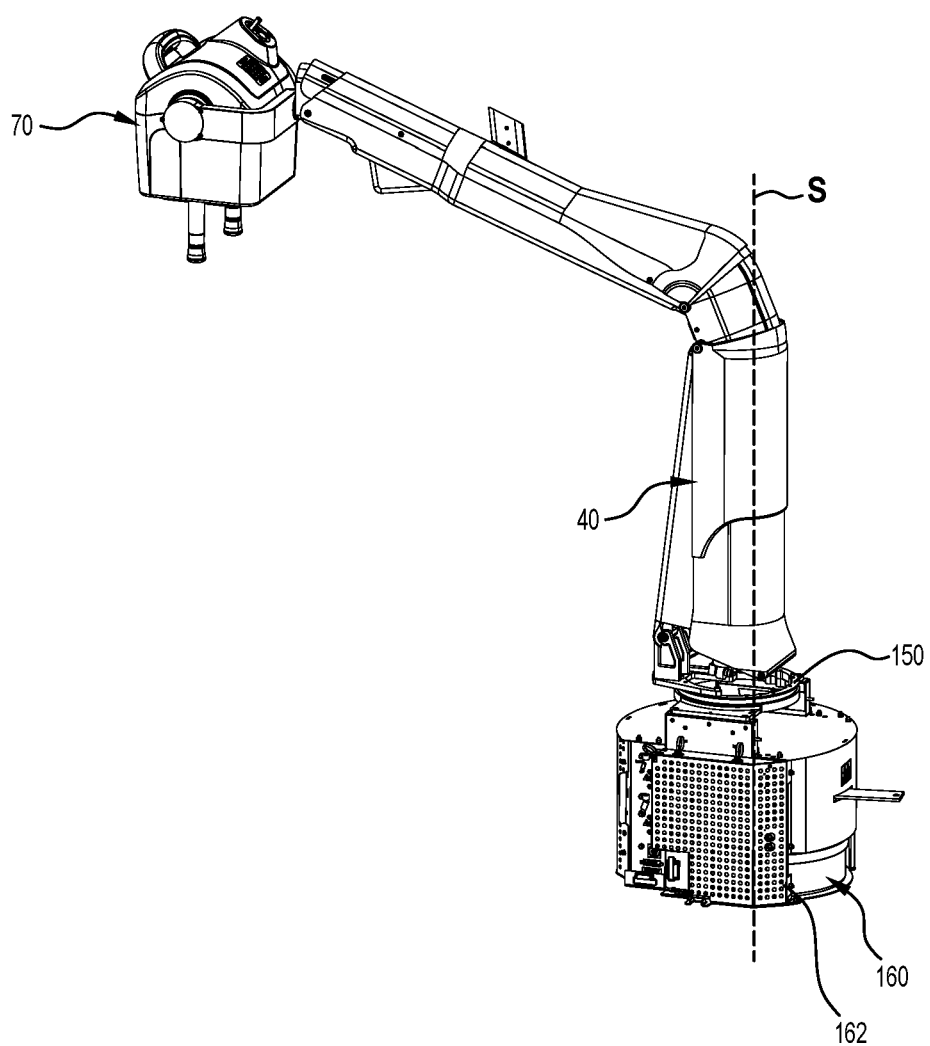
FIG. 23 is a perspective view of an assembly forming part of the cart, the assembly comprising the arm, the X-ray head, a yoke/mounting, via which the head is mounted to the distal end of the arm to be rotatable about perpendicular axes, a slew bearing via which a proximal end of the arm is rotatably mountable to a support/body section of the cart, and a generator unit which is arranged to be housed in the support/body section, is fixed with respect to the arm and depends from the slew bearing/arm proximal end.
Figure 24:
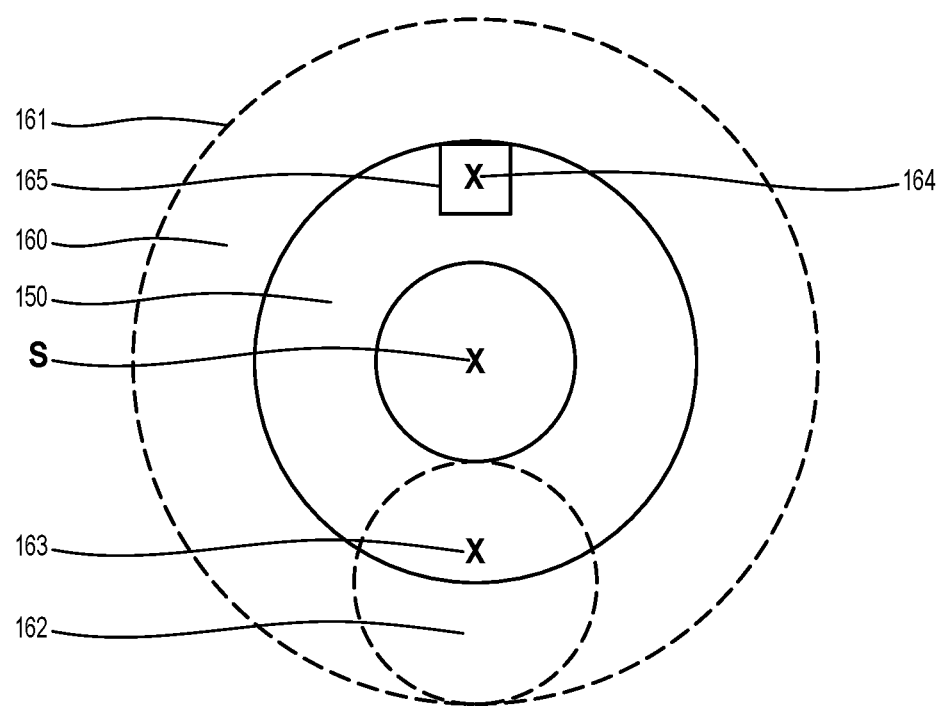
FIG. 24 is a schematic plan view of a layout of the slew bearing, generator unit, an oil tank of the generator unit and a position at which the arm connects to the slew bearing.
Figure 25:
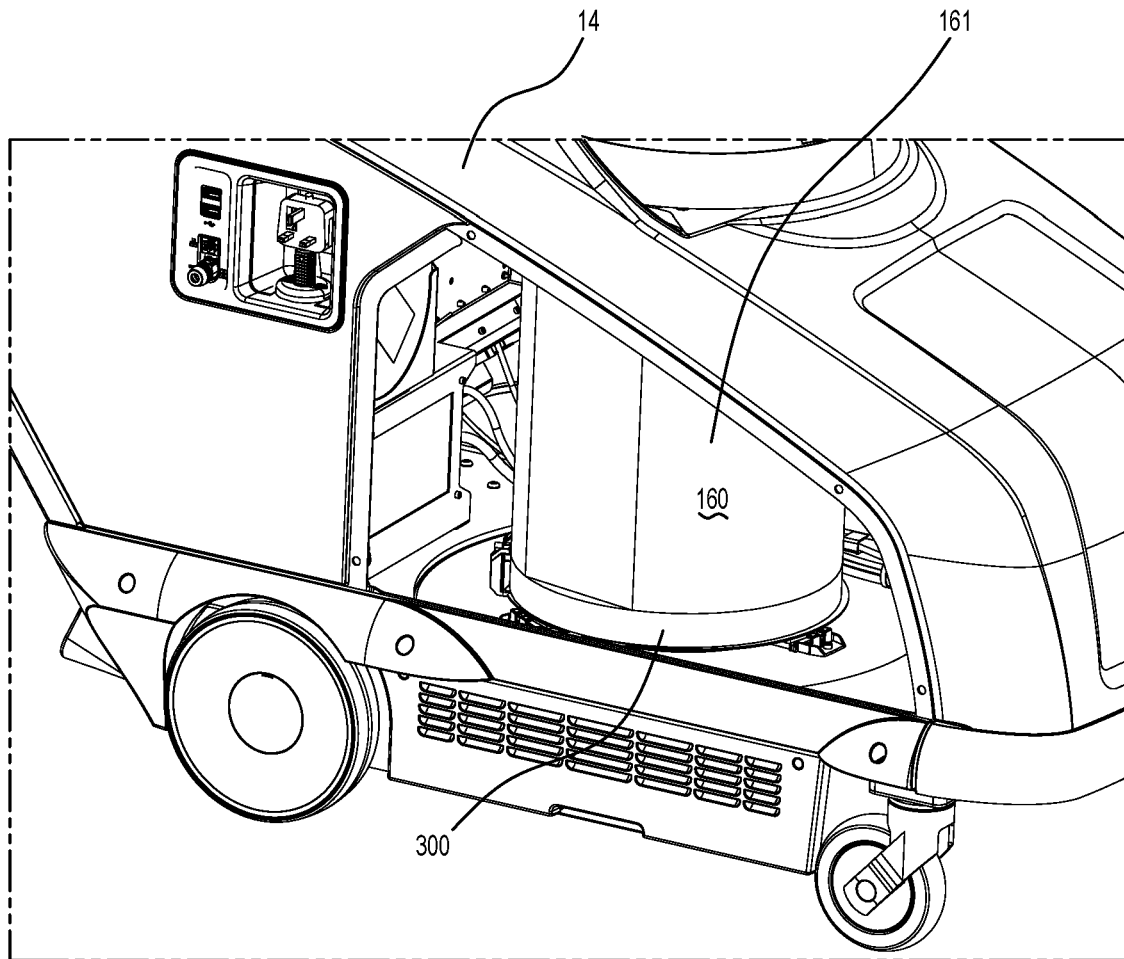
FIG. 25 is a perspective view showing the generator unit in situ, a further electrical cabling keeper of the cart which is arranged in a housing of the body/support section below the generator unit, and a removable cover, defining part of the housing, detached from the remainder of the housing such that the generator unit and further keeper.
Figure 26:
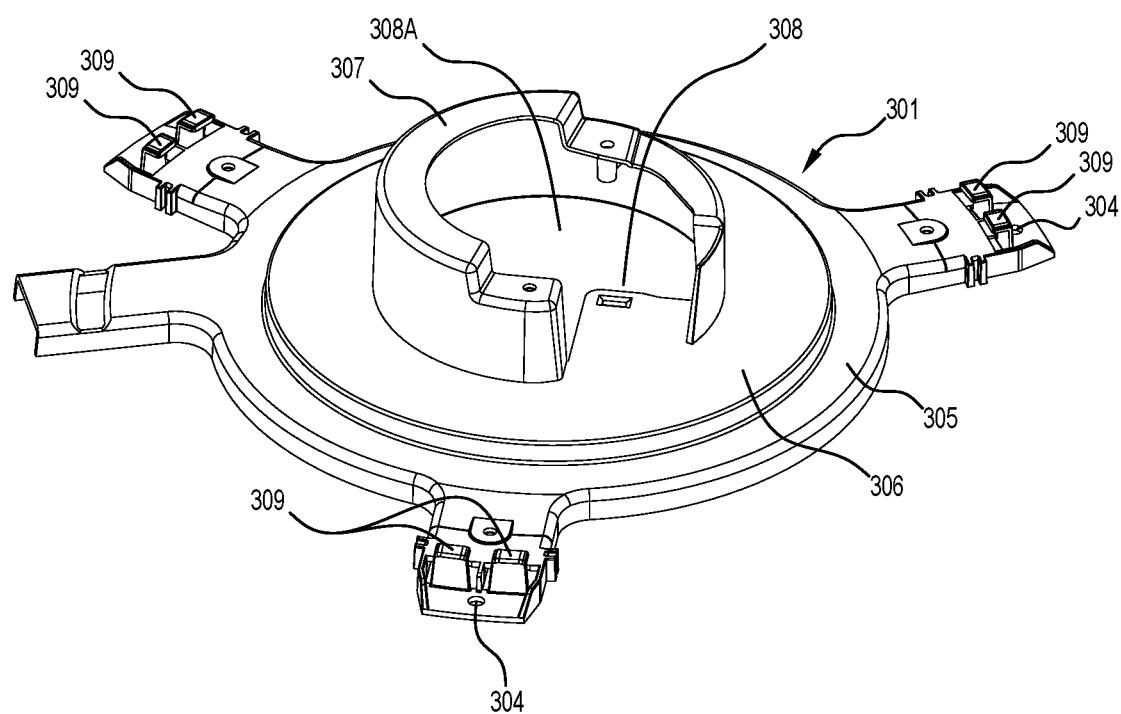
FIG. 26 is an upper perspective view of a base part of the further keeper.

Referring now to FIGS. 23 to 25, the cart 1 includes a slew bearing 150 which is secured to an exterior of the body housing 14 and to which a proximal end of the articulated arm 40 is connected (pivotally), whereby the arm 40 can be manually slewed relative to the body 10 about an axis S. The cart 1 additionally comprises a high-voltage generator unit 160 which is coupled, at an upper end thereof, to a rotatable part of the slew bearing 150 such that, when the arm 40 is slewed, the generator unit 160 rotates with the arm about the axis of the bearing 150. The generator unit 160 is arranged in the body housing 14 and most or all of the weight thereof is taken through the slew bearing 150, into the housing 14. The generator unit 160 comprises a housing or casing 161, a high-voltage (110 kV) generator contained within the housing/casing 161 and, associated with the generator, a tank 162 which, consistent with conventional generator tanks, contains oil in which is submerged a high-voltage connection to the generator. The housing 161 additionally accommodates other electrical components/cabling (not shown) of the cart 1. The oil makes up a significant proportion of the weight of the generator unit 160, and the tank 162, referring to FIG. 24, is eccentric to the slew axis S, such that the upright/vertical axis 163 (parallel to axis S) in which the centre of mass of the unit 160 lies is diametrically opposite, with respect to the slew bearing 150/axis S, to an upright/vertical axis 164, also parallel to axis S, passing through the position 165 at which the arm 40 is secured to the rotatable part of the slew bearing 150, such that the aforementioned centre of mass functions as a counterweight to offset the moment exerted on the body 10/wheels 12, 13 by the cantilevered arm 40 and head 70, whereby the resistance to toppling of the cart 1, as a result of that moment, is increased.

Figure 35:
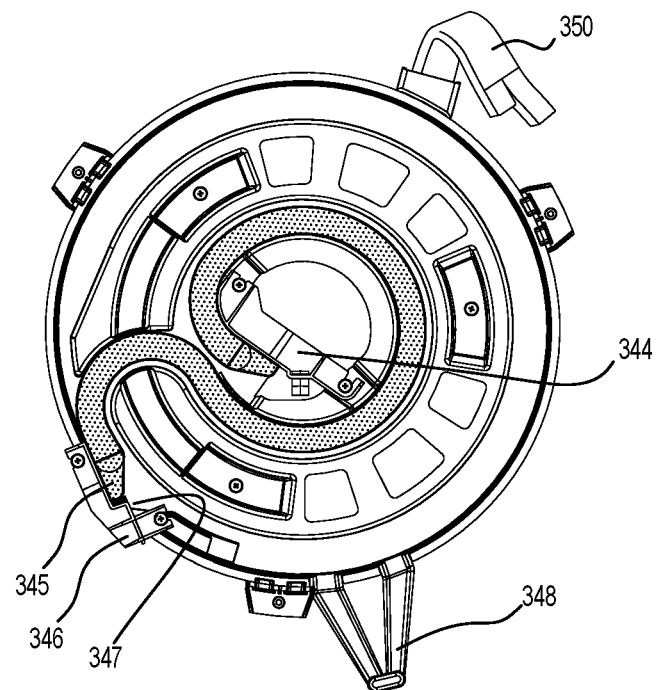
FIG. 35 is a plan view showing the arrangement of FIG. 32 in which the rotatable part has been rotated to a full rotational extent in a clockwise direction.
Figure 36:
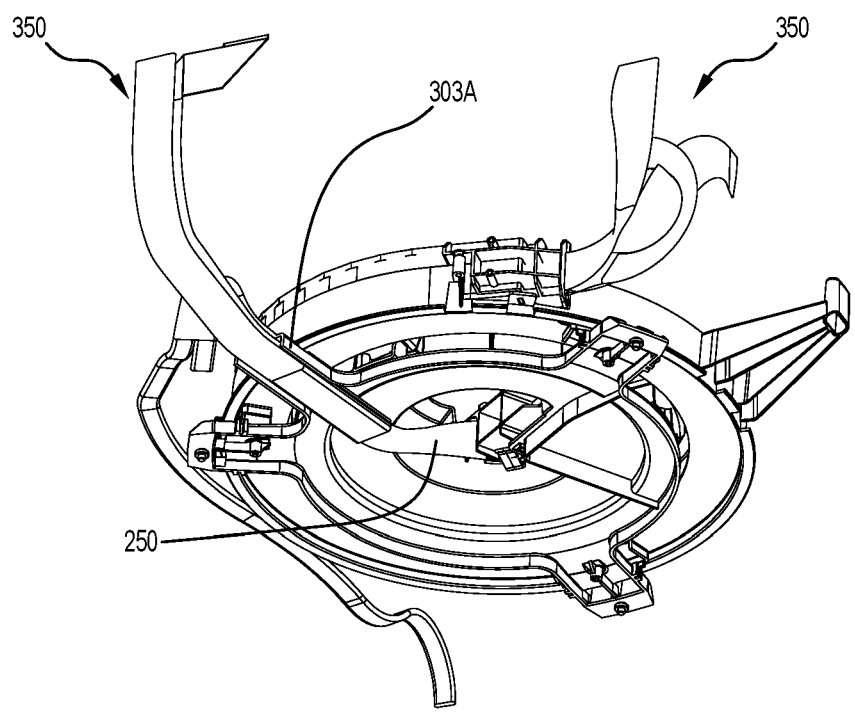
FIG. 36 is a lower perspective view showing details of the arrangement of FIG. 32.

Referring to FIGS. 25, 32, and 34 to 36, the cart 1 additionally comprises a keeper 300, arranged in the housing 14 below the generator unit 160. The keeper 300, referring also to FIGS. 26 to 31, 33A and 33B (each of which shows components of the keeper 300), comprises a base part 301, a peripheral part 310 which is interlockable with the base part 301 so as to be rotatable relative thereto, and a guide part 320 which is receivable by the rotatable part 310 so as to be rotatable relative thereto. Referring to FIG. 36, the cart 1 includes electrical cabling 350 which extends from the head 70, along the arm 4, through the central opening in the slew bearing 150 and into the housing 14, through the keeper 300, to a power control board (not shown) located in a rear part of the housing 14. The cabling 350 thus connects componentry which is fixed in the housing 14 (comprising the power control board) to componentry which is rotatable, about the slew axis S, relative to the housing 14. The keeper 300 operates to house a section of the cabling which at one end is fixed relative to the rotatable componentry (i.e. rotates with that componentry about the axis S), and at the other end is fixed with respect to the fixed componentry, and guides that section therewithin, during rotation of the arm 40 about the axis S, protecting that section, including in particular from snagging, during slewing of the arm 40.

Figure 27:
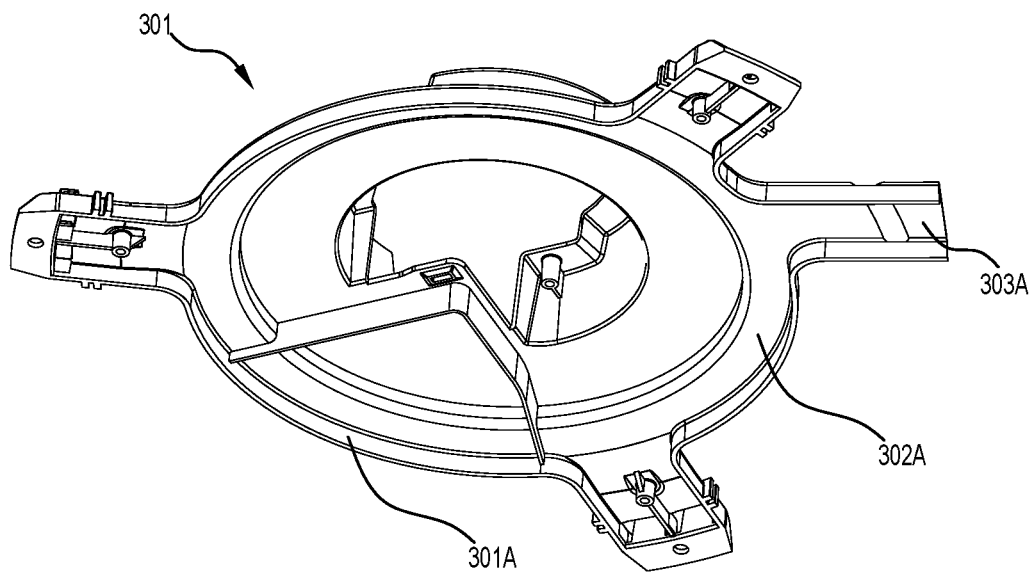
FIG. 27 is a lower perspective view of the base part.

The base part 301 comprises a base 302 which, when the keeper 300 is installed, is secured to a floor in the compartment within the housing 14. More particularly, the base 302 is fastened to the floor via fasteners received through mounting holes 304 therein. The base part 301 further comprises a circular floor section 305, supported on the base 302, the floor section 305 being configured with an annular shoulder 306. The base section 301 further comprises a central hub portion 307, open at upper and lower ends thereof, which projects upward from a radially inner part of the floor section 305. An opening 308 is formed through a side wall of the hub 307. The base part 301 further comprises L-shaped retainers 309, arranged at respective corner positions thereof, so as to engage slidably the rotatable part 310, as will be described in further detail shortly. As can be seen at FIG. 27, the base part 301 includes a downwardly projecting peripheral wall portion 301A whereby there is defined cavity 302A for containing part of the cabling 350, as will be described in further detail shortly. The base part 301 further includes a radially outwardly projecting mouth section 303A, which defines part of the cavity 302A, the mouth section being arranged to house a section of the cabling which adjacent the position at which it enters/exits the cavity 302A.

Figure 28:
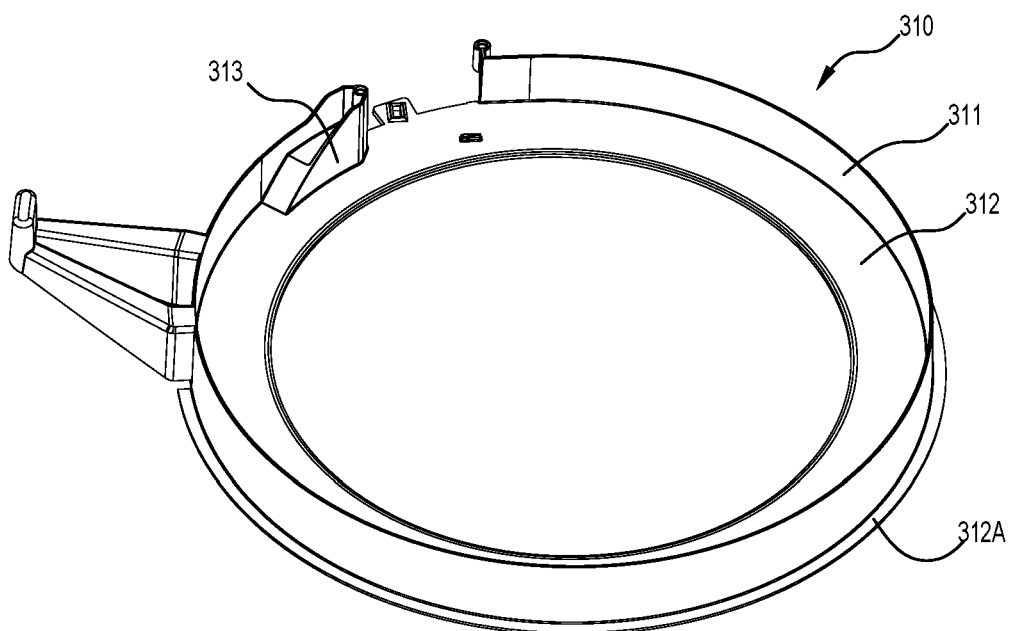
FIG. 28 is a lower perspective view of a rotatable part of the further keeper.
Figure 29:
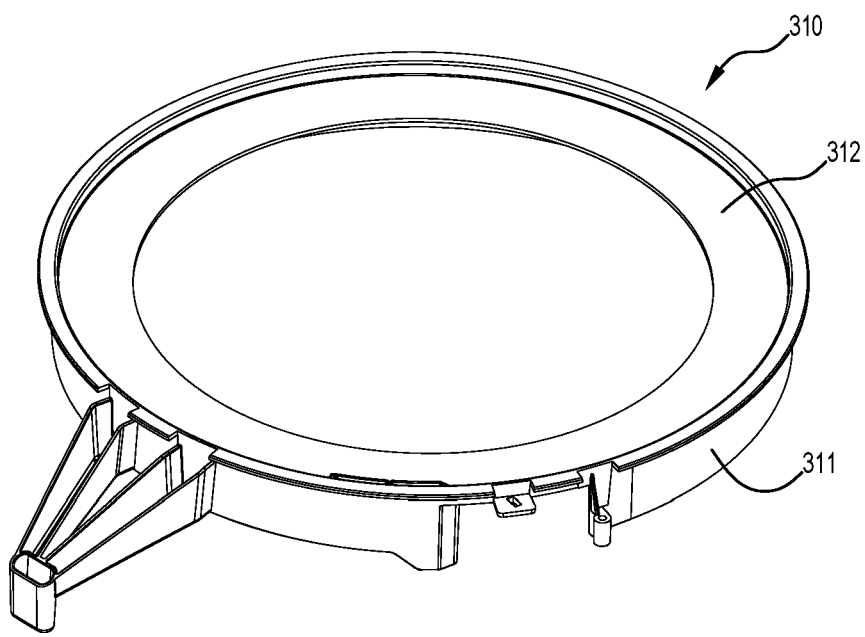
FIG. 29 is an upper perspective view of the rotatable part.
Figure 30:
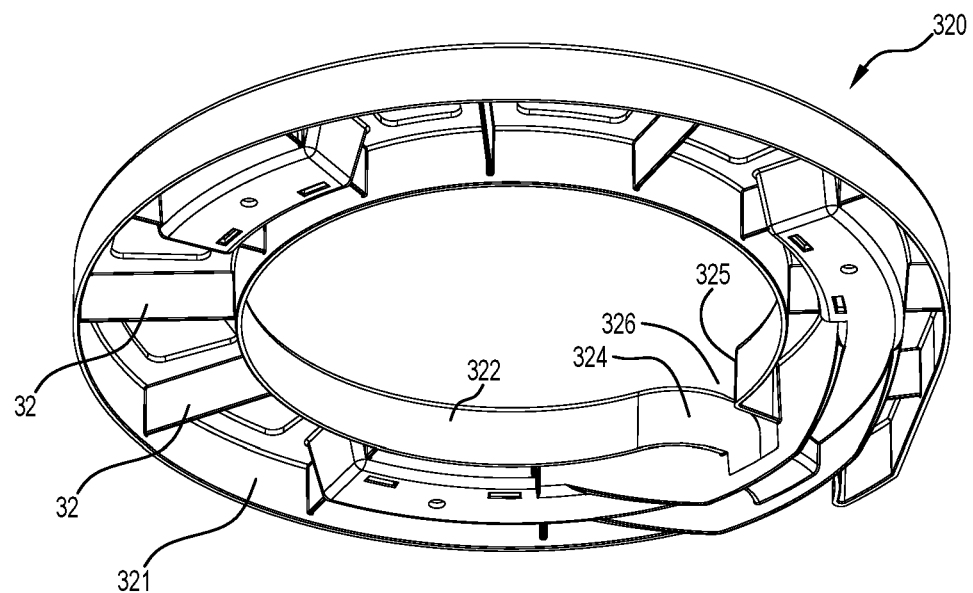
FIG. 30 is an upper perspective view of a guide part of the further keeper.
Figure 31:
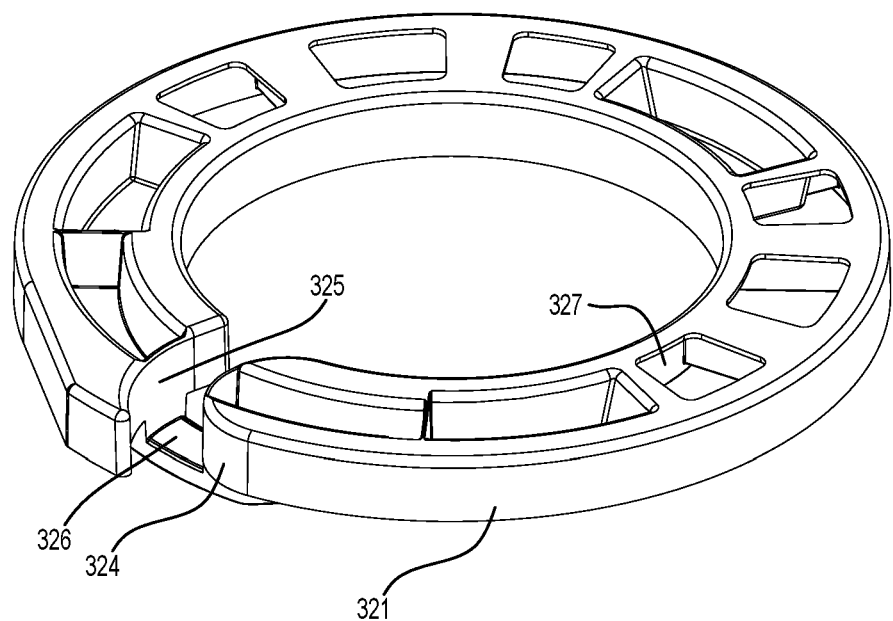
FIG. 31 is a lower perspective view of the guide part.

Referring in particular to FIGS. 28 and 29, the rotatable part 310 comprises a circumferential side wall 311 and an annular floor section 312 which extends radially inwardly from a lower end of the wall 311. The retainers 309 are resiliently flexible whereby they can be bent radially outwardly such that the rotatable section 310 is downwardly introducible onto the base section 301 and the underside of the rotatable part annular floor section 312 thus rests against the base part floor section 305 radially outward of the shoulder 306. Allowing the retainers 309 to resile to their relaxed positions results in radially inwardly projecting upper ends thereof being received over an annular rim portion 312A of the section 310, precluding upward displacement of the section 310 relative to the section 301. The housing section 310, thus received by the base section 301, can rotate about an upright axis extending centrally through the opening through the top of the hub portion 307, whereby the underside of the housing part floor section 312 slides against the upper face of the base part floor section 305. The peripheral part 310 is additionally configured with a curved retainer portion 313 which extends radially inwardly from the wall 311 and upwardly from the floor section 312 and is positioned to abut slidably the radially outer circumferential face of the guide 320, so as to assist in retaining the guide 320 such that its axis of rotation and the axis of rotation of the peripheral part 310 are coaxial.

The guide part 320 comprises a radially outer circumferential side wall 321, a radially inner circumferential side wall 322 and a plurality of spaced apart radial ribs 323 interconnecting the walls 321 and 322. The guide part 320 is configured with a convex upright face 324 and, spaced from and extending substantially parallel to that face, a concave face 325, the faces 324 and 325 defining side faces of a curved channel 326 which, at a radially outer end thereof, opens through the wall 321 and, at a radially end thereof, opens through wall 322. The guide part 320 further includes, at a lower end thereof, a downwardly projecting circumferential rib 327, defined by a downwardly projecting lower portion of the wall 322, which is of a diameter such that, when the guide part 320 is supported on and coaxial with the floor section 305 of the base part 301, the rib 327 engages the shoulder 306, whereby the guide section 320 is retained rotationally on the floor section 305.

Figure 32:
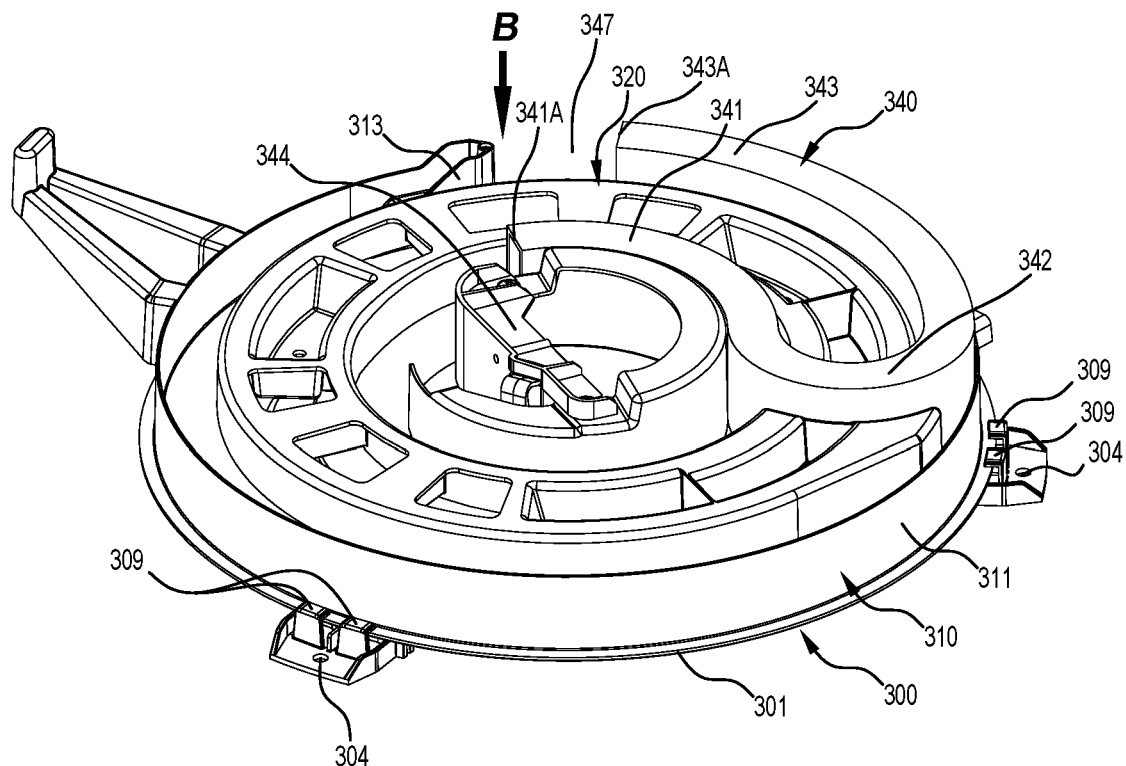
FIG. 32 is an upper perspective view of the further keeper in the configuration it assumes in situ and electrical cabling of the cart, to which tubular conduit is applied, trained therethrough.
Figure 33A:
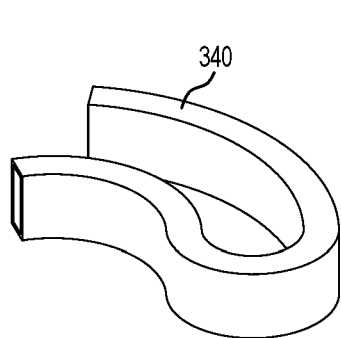
FIG. 33A is an upper perspective view of the tubular conduit assuming the configuration thereof which is shown in FIG. 32.
Figure 33B:
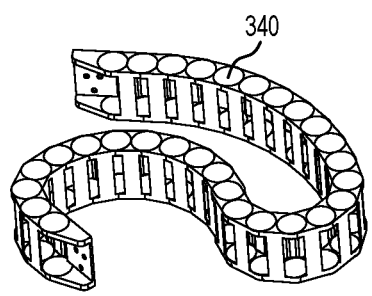
FIG. 33B is an upper perspective view of chain conduit which may be used in the keeper instead of tubular conduit.
Figure 34:
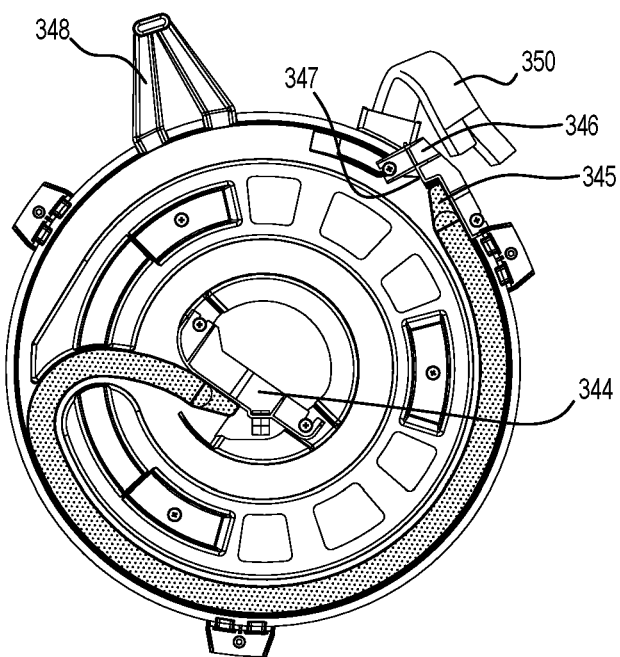
FIG. 34 is a plan view showing the arrangement of FIG. 32 in which the rotatable part has been rotated to a full rotational extent in an anticlockwise direction.

The keeper 300 further comprises a conduit 340, configured in the form of a curved, slender tube which is rectangular in cross-section, the tube thus substantially assuming, or its dimensions approaching, the proportions of a "strip". Referring to FIG. 32, in the assembled keeper 300, the conduit 340, with the cabling 350 trained therethrough, is positioned in the housing defined by the rotationally coupled base section 301 and peripheral section 310, whereby there is a portion 341 of the conduit/cabling which extends in a radially inner channel defined between the hub side wall 307 and the guide inner circumferential wall 322 (a base of which channel is formed by the floor section 305), a portion 342 of the conduit/cabling which extends through the channel 326, and a portion 343 of the conduit/cabling which extends through a channel defined between the peripheral part circumferential side wall 311 and the outer circumferential side wall 321 of the guide 320 (a floor of that channel being defined by the annular portion 312 of the peripheral part 310). The keeper 300 includes a connector 344 which secures, to the hub portion 307, the conduit end 341A positioned in the radially inner annular channel, and a connector 345 which secures, to the peripheral part annular sidewall 311, the conduit end 343A which is positioned in the radially outer annular channel, the conduit ends 341A and 343A thus being fixed relative to the base part 301 and peripheral part 310 respectively. The keeper 300 further comprises a retainer 346 which is removably attached to the peripheral part 310 and serves to hold the cabling 350 in place adjacent a position at which it enters the housing defined by the parts 301 and 310, the cabling 350 passing downwardly (as shown by the arrow B in FIG. 32) into an entrance section 347 with which the peripheral part 310 is configured. The peripheral part 310 is configured with a tab or projection 348 configured to be fixed to the generator housing 161 when the keeper 300 is installed below the generator 160 as shown in FIG. 25, whereby the peripheral part 310 rotates with the housing 161 when the arm 40 is slewed. The keeper 300 is dimensioned such that the cabling 350 fits snugly or is arranged confinedly between the radially opposed walls of the radially inner and outer channels, such that it is braced radially/laterally in each of those channels and thus cannot buckle in either of those channels, and, and also fits snugly or is arranged confinedly between the faces 324 and 325 so that it is braced laterally in the channel defined between those faces and thus likewise cannot buckle.

Sections of the cabling 350 extend from inside the keeper housing, through the hole 308 in the hub section sidewall and central hole 308A through the hub section 307. FIG. 32 shows the keeper in one of two opposite extreme rotational conditions which it can assume. Specifically, the condition shown in FIG. 32 is that in which the peripheral section 310 has been rotated anticlockwise as far as possible with respect to the base section 301, the position shown corresponding to the articulated arm 40 having been slewed to the maximum extent possible in an anticlockwise direction (as viewed from above). Slewing of the arm 40 in the clockwise direction imparts clockwise rotation to the generator 160, and thus, through the tab 348, to the keeper peripheral part 310. The end 343A of the conduit thus rotates, in a clockwise direction, with the peripheral part 310, while the conduit end 341A remains stationary, with the result that the conduit 340 slides, in a radially inward direction, through the radial channel 326, the (constantly changing) curved portion 342 thereof thus pushing on the concave channel face 325 such that the guide part 320 also rotates clockwise, though at half the rotational speed of the peripheral part 310.

The cabling 350 may comprise strip cable, as shown, or individual cables side by side.

Without departure from the invention, the conduit, instead of being configured in the form of a flexible/pliable tube 340, may be one which is comprised of interconnected articulating sections; for example, it may comprise chain conduit 340' shown in FIGS. 35 and 36, the chain of the conduit comprising links through which the cabling 350 is passed. FIG. 35 shows the "anticlockwise-most" position of the peripheral part 310, corresponding to FIG. 32, whereas FIG. 36 shows the "clockwise-most" position of the peripheral part 310.

It will be noted that, as the peripheral part 310 rotates clockwise, the length of the section 341 occupying the inner annular channel progressively increases, while the length of the section 343 occupying the radially outer annular channel progressively reduces.

Slewing of the arm 40 back in the anticlockwise direction imparts clockwise rotation to the generator 160, and thus, through the tab 348, to the keeper peripheral part 310. The end 343A of the conduit thus rotates, in an anticlockwise direction, with the peripheral part 310, while the conduit end 341A remains stationary, with the result that the conduit 340 slides, in a radially outward direction, through the radial channel 326, the (constantly changing) curved portion 342 thereof thus pushing on the convex channel face 324 such that the guide part 320 also rotates anticlockwise, though at half the rotational speed of the peripheral part 310.

The keeper 200 in the X-ray head 70 is correspondingly configured, the fixed and rotatable components between which it is interposed comprising the X-ray source 71 and shield/collimator assembly respectively, though the cabling in the case of that keeper, defined by the strip cable 201, is unified so that conduit of the kind used in the keeper 300 is unnecessary and omitted (abutment of the cabling against the guide part radial channel curved faces (to rotate the guide part) thus being direct). Referring again to FIG. 14 the corresponding "peripheral part", shown by reference numeral 210, of the keeper 200 is configured with a tab 248 which engages part of a frame structure on which the X-ray source 71 is fixed, so as to hold the peripheral section 201 stationary.

Details of the arm assembly are shown in FIGS. 6 to 11. The arm 40 in that assembly comprises a proximal arm section 410 and a distal arm section 460. The arm 40 is provided with an exterior casing or cladding 41 comprising sections movable relative to one another to permit articulation of the arm whilst precluding access to a linkage arrangement forming part of the arm 40. The linkage arrangement is shown at FIGS. 7A and 8 to 11 (from which details of the cladding/casing 41 are omitted).

The proximal arm section includes a first elongate linkage 411, comprising a carbon fibre member of generally U-shaped transverse cross-section, and a parallel second elongate linkage 412, the proximal ends of each of which are connected to a base 413 of the arm assembly (which base is fixably securable to the rotational part of the slew bearing), via spaced apart pivots 414 and 415 respectively, so as to be pivotable about respective parallel axes. The arm 40 further comprises an intermediate linkage 480 to a proximal end 482 of which distal ends of the linkages 411, 412 are connected at spaced apart positions, via pivots 416 and 417 respectively, the axes of the pivots 416 and 417 being parallel to the axes of the pivots 414, 415 (and, more particularly, horizontal). The distal arm section 460 likewise comprises a first elongate linkage 461, comprising a carbon fibre member of generally U-shaped transverse cross-section, and a parallel second elongate linkage 462, proximal ends of which linkages are connected to a distal end 484 of the intermediate linkage at spaced apart pivots 466 and 467 respectively. The linkages 461 and 462 are thus able to pivot relative to the intermediate linkage 480 about respective axes each of which is parallel to the axes of the pivots 414, 415. The arm further includes an end linkage 490 (see FIG. 9) pivotally connected at one end to a distal end of the linkage 461 at a pivot 461A and pivotally connected at the other end thereof to a distal end of the second elongate linkage 462 at a pivot 462A. Referring to FIGS. 1 and 2, the cart includes a yoke 500 connected to the end linkage 490, whereby the head is rotatable, relative to the distal section of the arm 40 about orthogonal axes F and G.

The proximal arm section 410 includes a tension redirector. More particularly, that section includes a linkage 430 pivotally connected at a proximal end thereof to the base section 413, and a collar 431 which is received over the linkage 412 and is pivotally connected to a distal end of the linkage 430. The proximal section 410 additionally includes a pair of springs 432A and 423B, arranged end-to-end over the linkage 412 and between the collar 431 and a stopper secured to a lower part of the linkage 412. The section 410 further includes a collar 433, which is received over the linkage 412 and arranged between the springs 432A and 423B. When the arm section 410 pivots from a substantially upright orientation (shown in FIG. 7A) towards the slew axis S, the collar 431, as can be seen in FIGS. 8 and 9, is displaced towards the proximal end of the linkage 412, compressing the springs 432A, 432B whereby the arm section 410 is biased, to a progressively increasing degree, against gravity during its pivoting/rotation, whereby the proximal section is configured with a tension redirector. As the degree to which the arm section 410 has been so rotated/pivoted becomes relatively extreme, the spring 432A approaches a fully compressed condition and the rate of compression of the second spring 432B, which is stiffer than the spring 432A, increases, the spring 432B thus contributing a relatively large biasing force against the continued pivoting/rotation, under gravity, of the arm section 410.

Figure 7A:
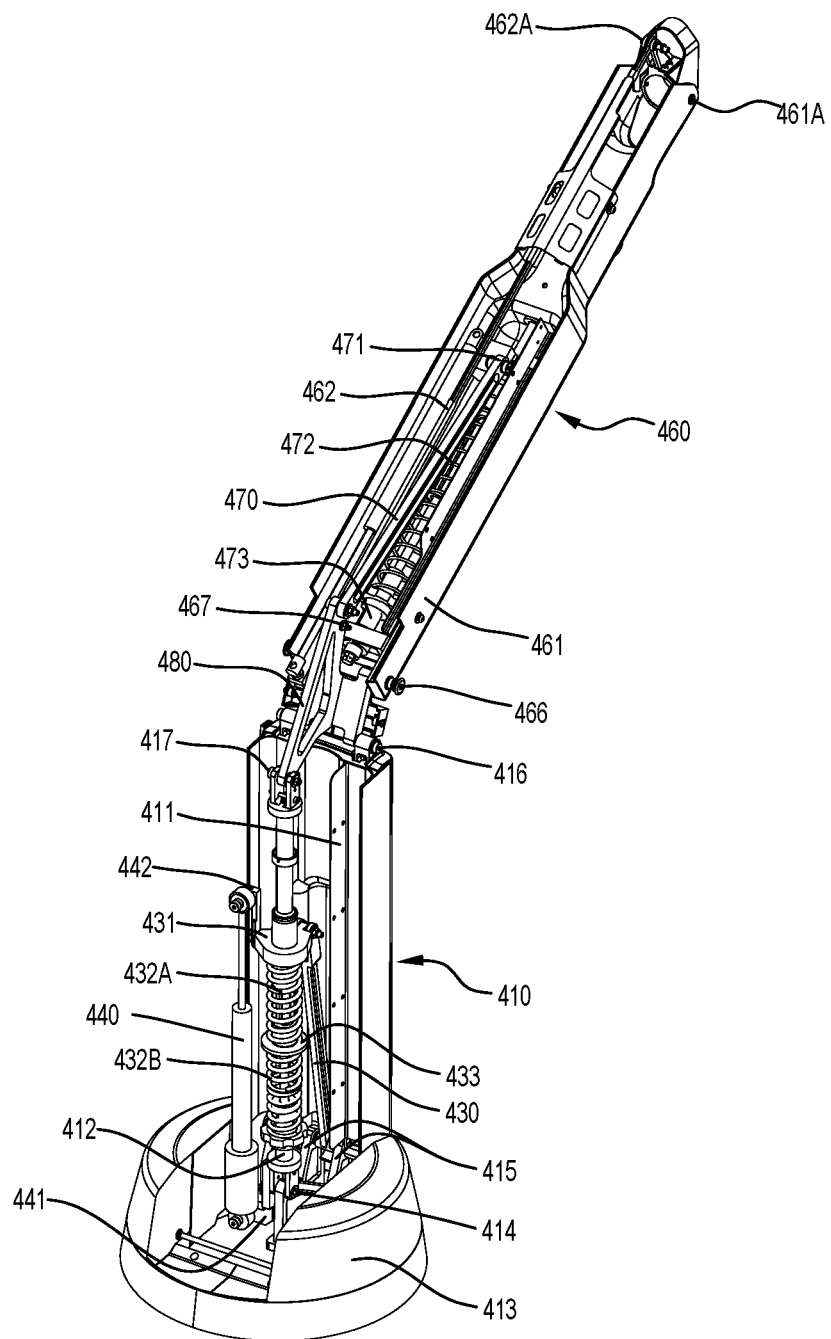
FIG. 7A is a perspective view showing details of the arm assembly (in which parts of the assembly are omitted for clarity)
Figure 7B:
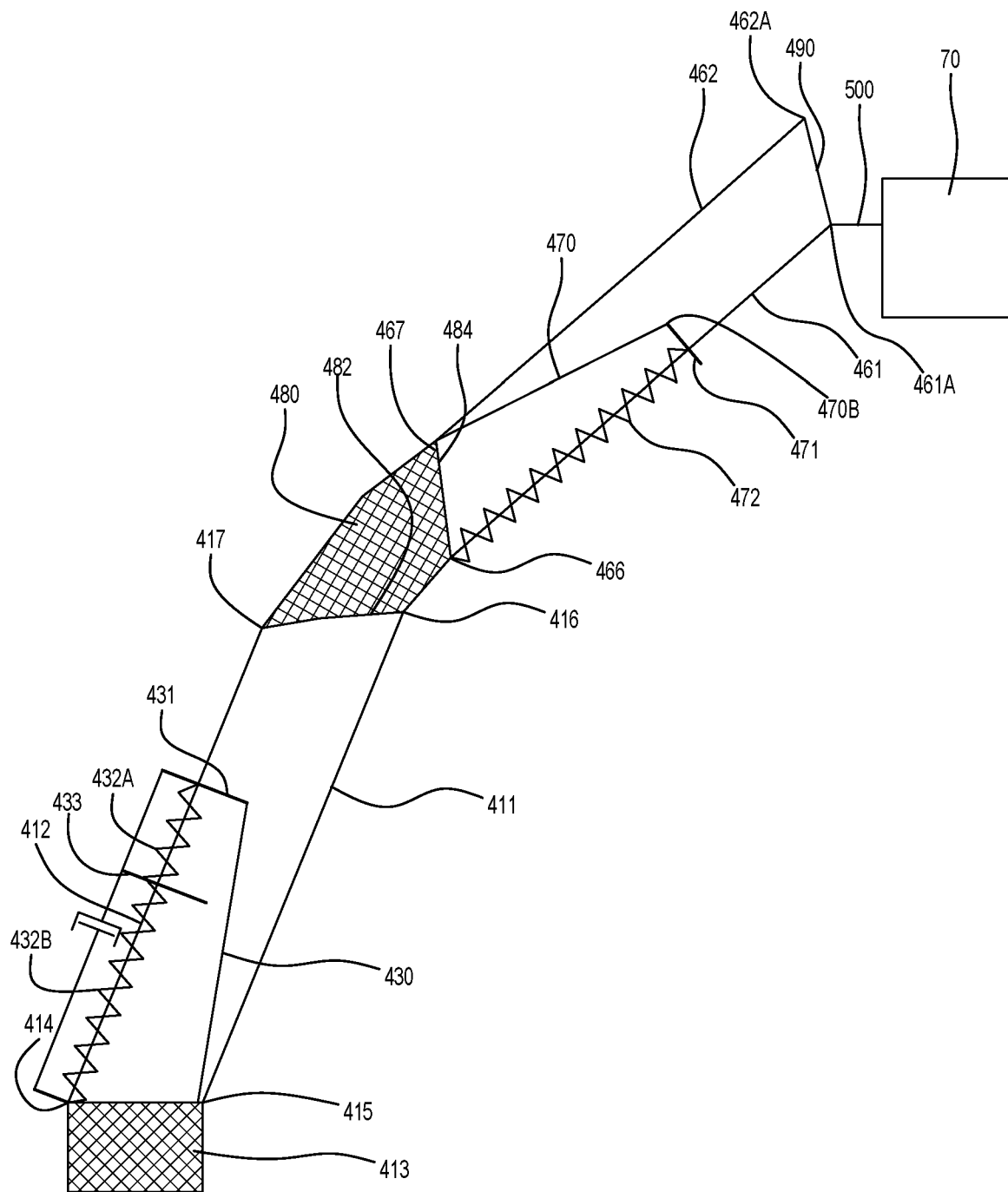
FIG. 7B is a stick/schematic diagram showing a linkage, tension adjustor and damper arrangement of the arm assembly.
Figure 7C:
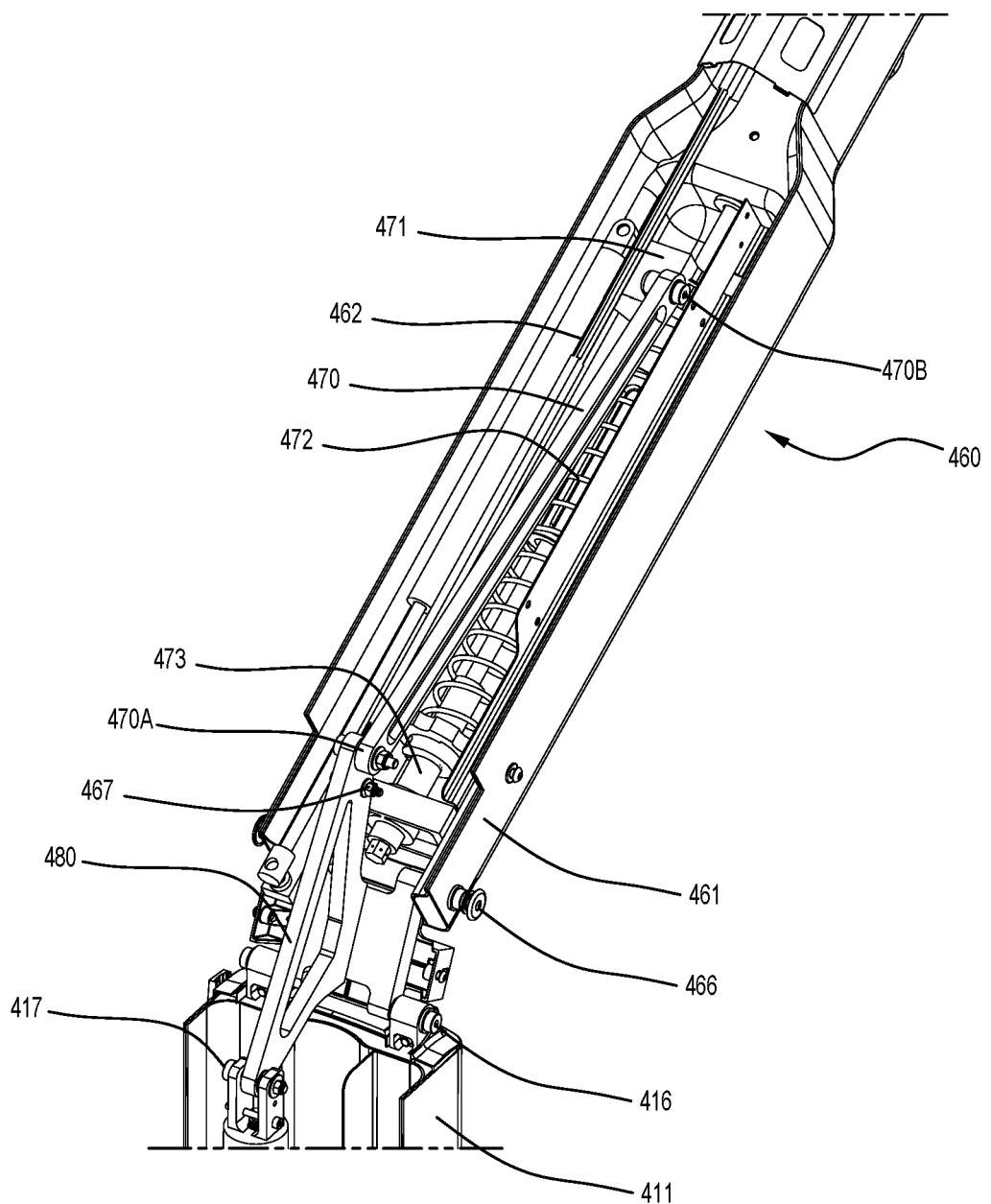
FIG. 7C is a detail view showing part of what is shown in FIG. 7A.
Figure 8A:
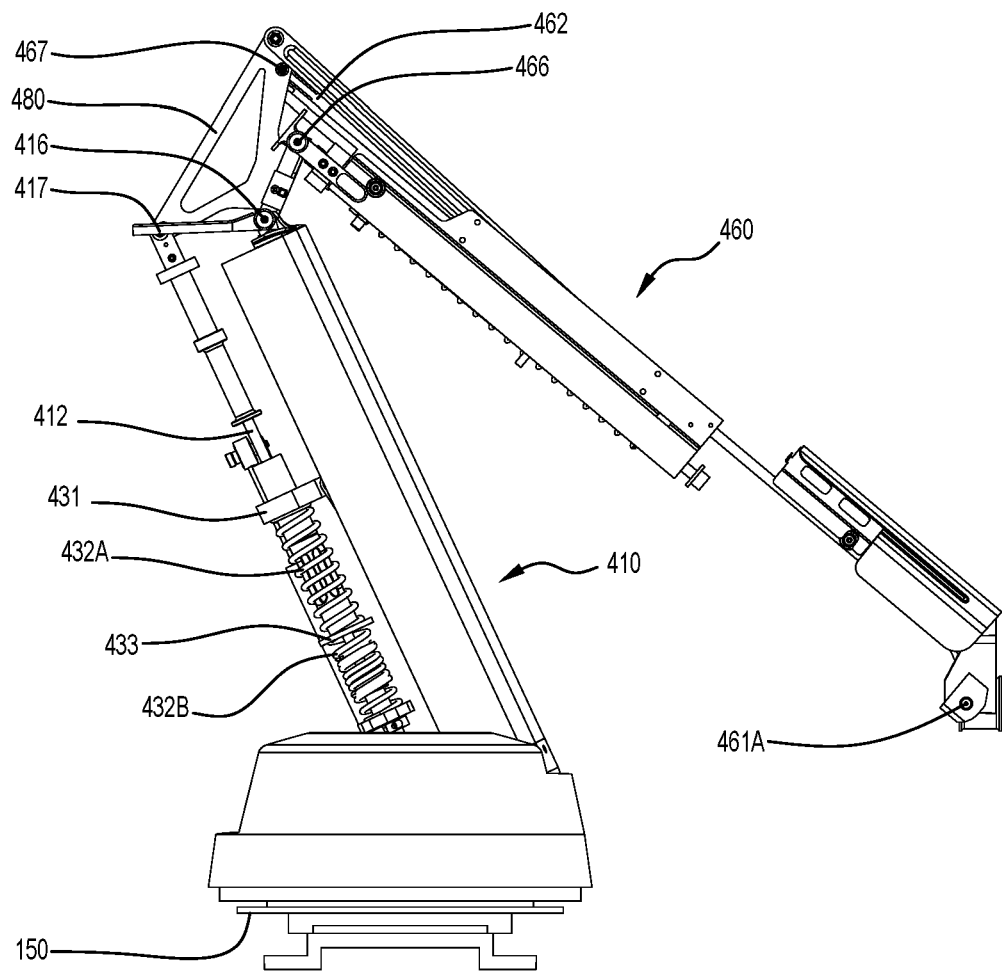
FIGS. 8A and 8B are side views showing details of the arm assembly in a first configuration (in which parts of the assembly are omitted for clarity)
Figure 8B:
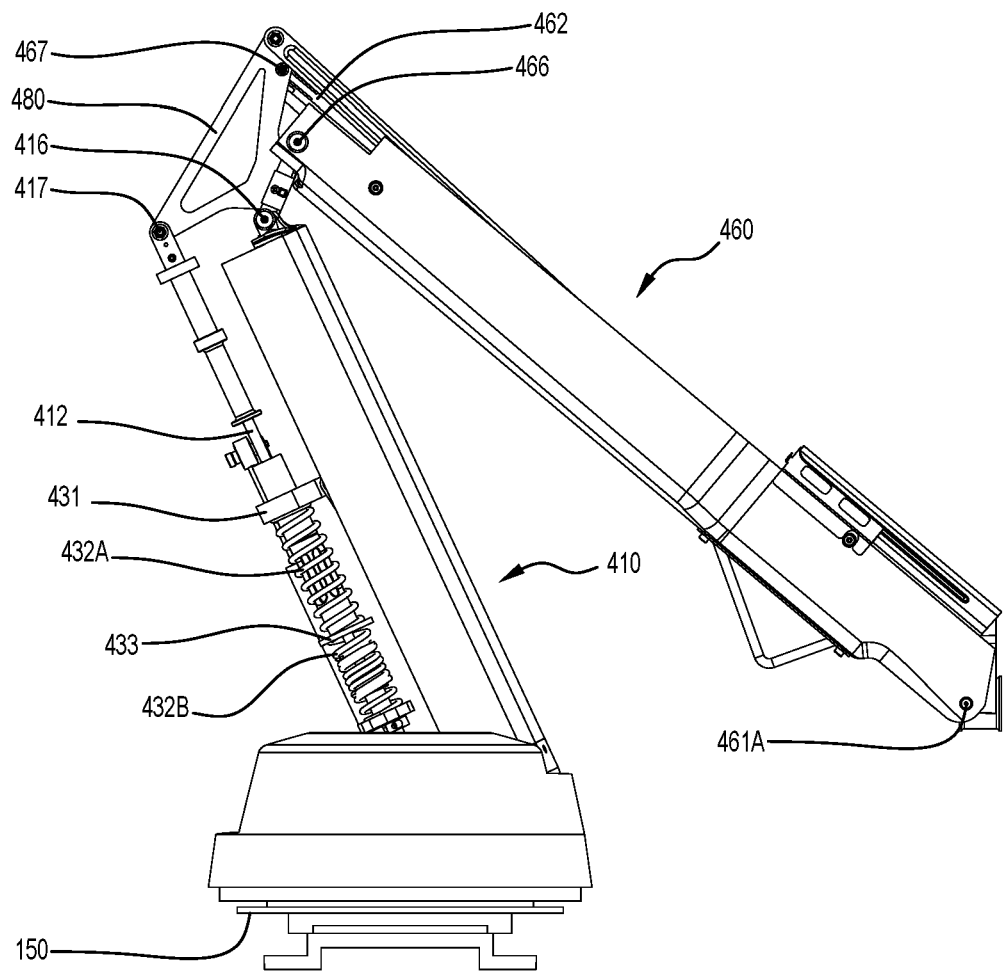
Figure 9A:
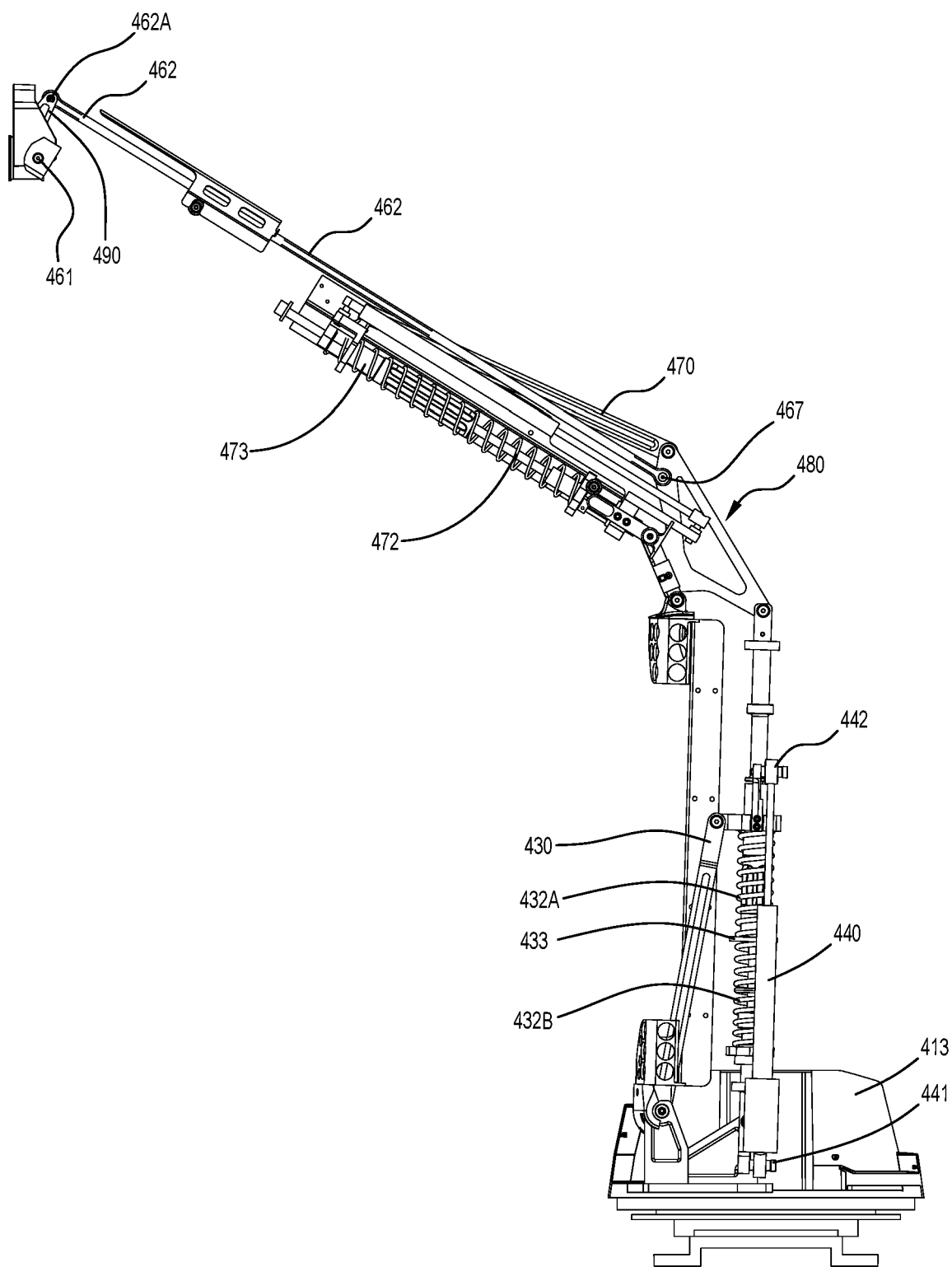
FIGS. 9A and 9B are side views showing details of the arm assembly in a second configuration (in which parts of the assembly are omitted for clarity)
Figure 9B:
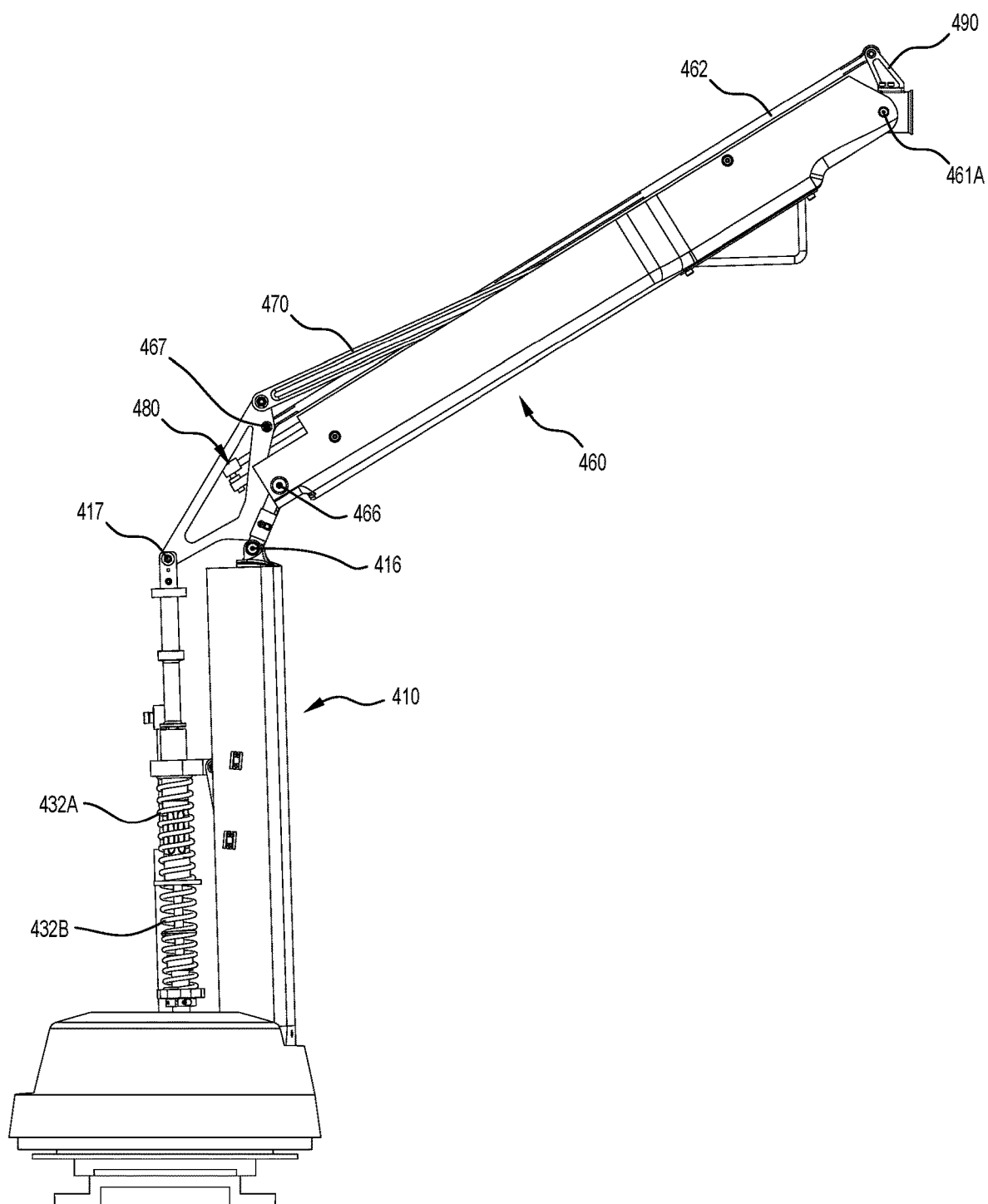
Figure 10:
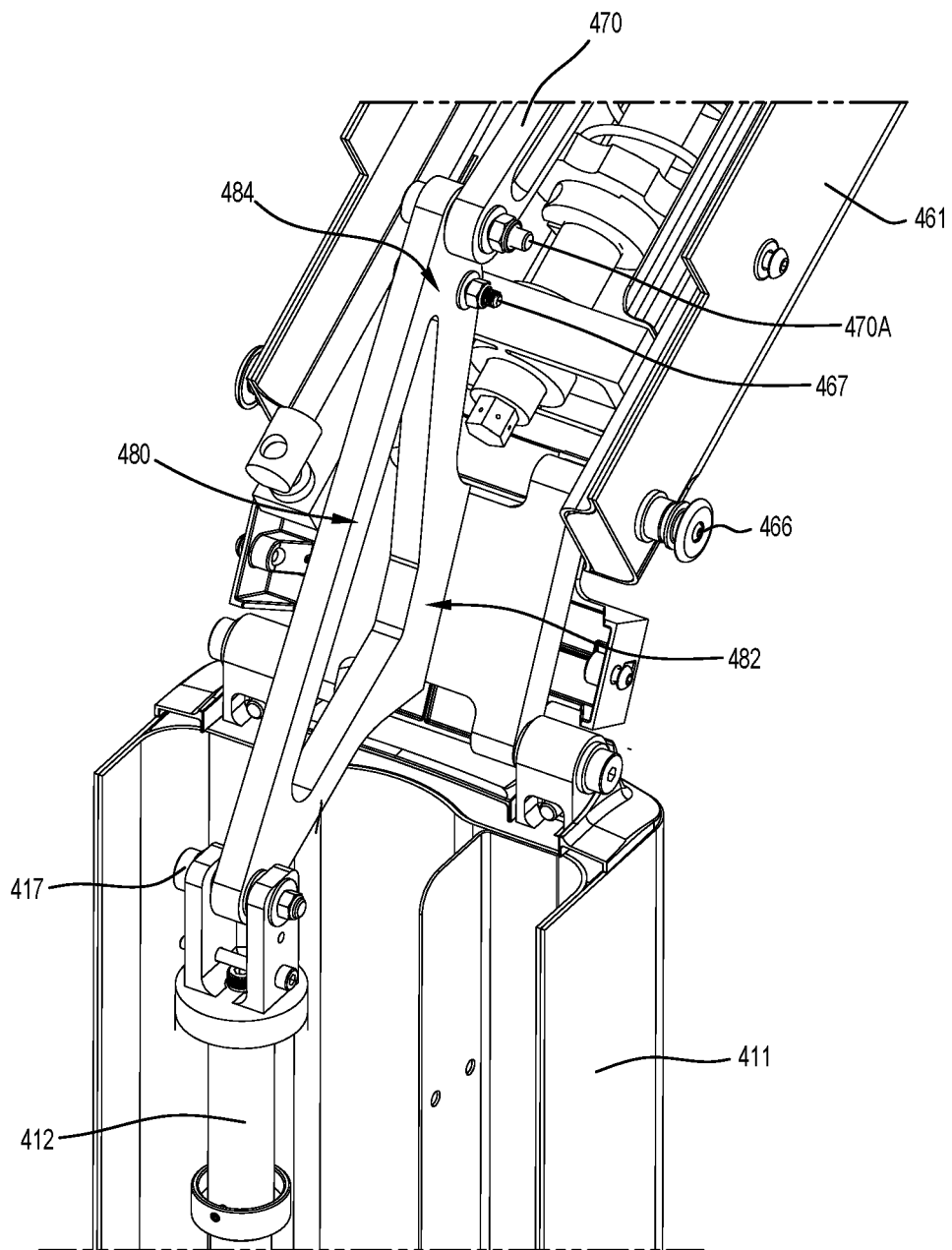
FIG. 10 is a perspective view showing an arrangement of linkages in the assembly, including an intermediate linkage, forming part of a collapsible elbow of the articulated arm, in a first condition (in which parts of the assembly are omitted for clarity)
Figure 11:
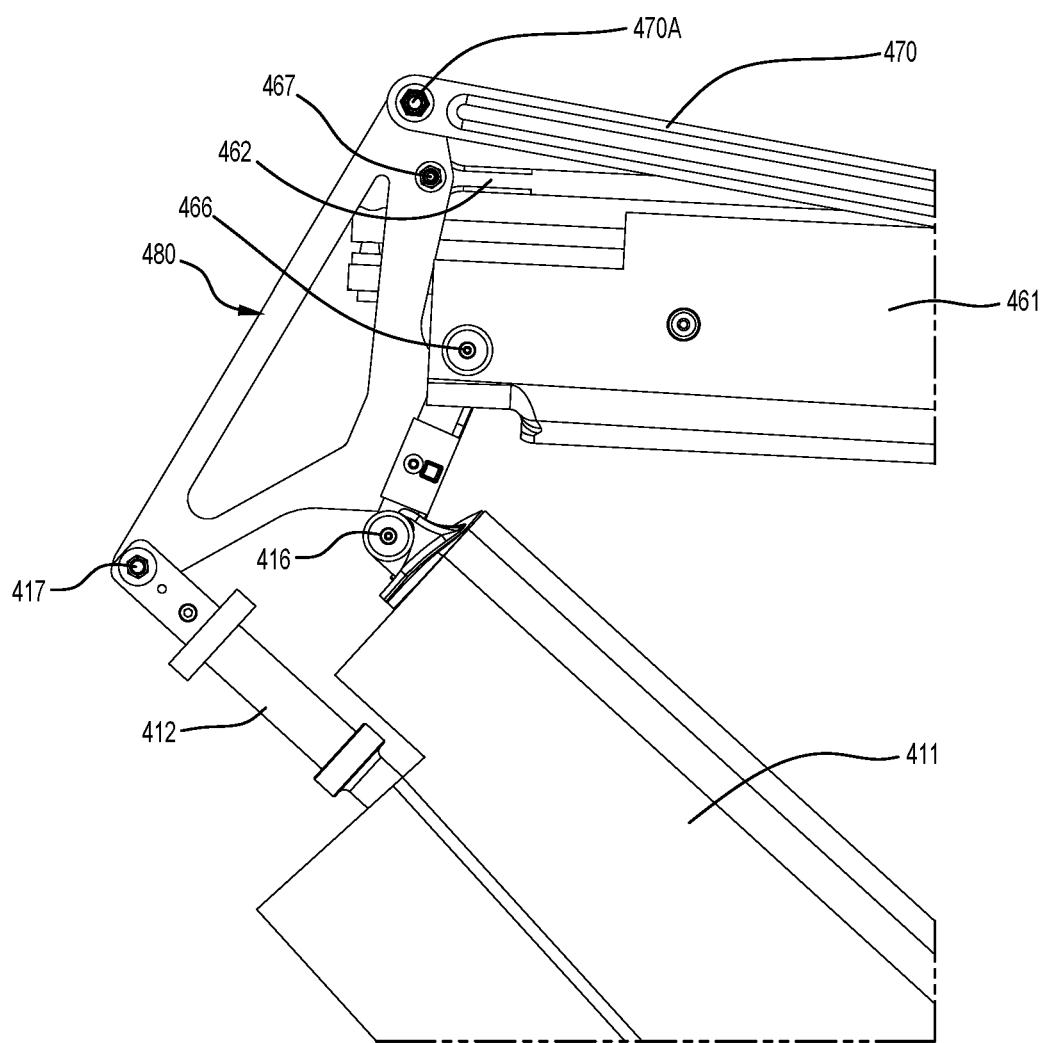
FIG. 11 is a side view of the arrangement shown in FIG. 10, in a second condition (in which parts of the assembly are omitted for clarity)
Figure 12:
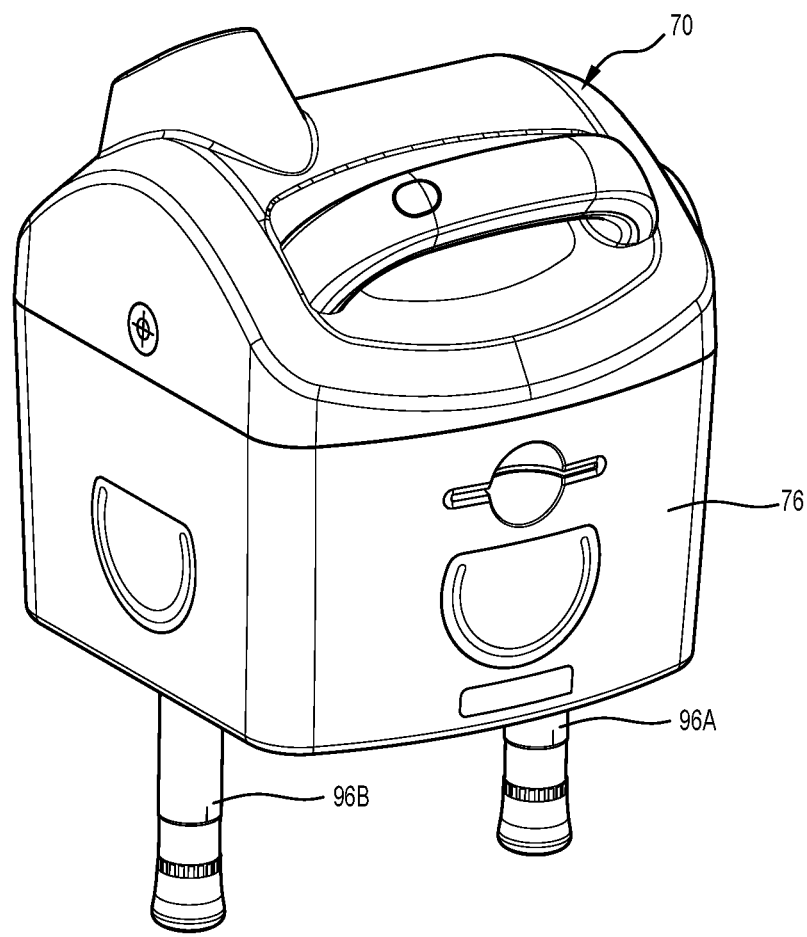
FIG. 12 is a front perspective view of an X-ray tube head of the cart.

Referring to FIGS. 7A and 9A, the arm section 410 further includes a damper 440, preferably an oil damper, which extends (and remains) parallel to the linkage 412 and is connected at a proximal end thereof, via a bracket 441, to the lower end of the linkage 412, and connected at a distal end thereof, via a bracket 442, to the collar 431. The damper 440

The cart 1 of the illustrated embodiment is configured to preclude the arm section 410 from pivoting appreciably in the opposite direction from the generally upright orientation shown in FIG. 7A; for example, it may be configured with a hard stop (not shown) which is arranged to abut the section 410 to obstruct such pivoting. Alternatively, the arm section 410 may be able to pivot appreciably in that opposite direction, in which case the proximal arm section 410 will further include an upper spring arranged over the linkage 412 and between the collar 431 and a stopper secured to an upper part of the linkage 412, such that when the arm section 410 is pivoted/rotated in that opposite direction, the collar 431 is displaced upwardly along the linkage 412, so as to compress the upper spring, such that continued rotation of the proximal section 410 is resisted, to a progressively increasing extent as the effect of gravity on that section increases. The lower springs 432A and 432B and collar 431 could, without departure from the invention, be replaced with a single lower spring received over linkage 412.

The distal arm section 460 likewise has a corresponding tension redirector. The tension redirector comprises a linkage 470 pivotally connected, via a pivot 470A, at a proximal end thereof to the intermediate linkage 480, and pivotally connected, via a pivot 470B, at a distal end thereof to a collar 471 which is received over a shaft 473 forming part of the distal arm section first elongate linkage 461. A spring 472 is arranged over the shaft, between the collar 471 and a stopper secured to a proximal end portion of the shaft 473. Rotation of the distal arm section 460, beyond the orientation thereof (with respect to the proximal arm section 410) shown in FIG. 7A, in a direction such that the included angle between the arm sections 410, 460 (shown to be approximately 90 degrees in FIG. 7A) reduces, causes the collar 471 to be displaced towards the proximal end of the shaft 473 such that it compresses the spring 472, whereby the spring 472 offers a progressively increasing resilient bias against continued rotation of the distal arm section 460 under the progressively increasing influence of gravity. As a result, the arm 40, with the head 70 attached thereto is stable in any of the orientations and conditions into which it can be placed when in situ, exemplary such orientations/conditions being shown in FIGS. 6 to 11.

Owing to the linkage arrangement in the arm 40, the orientation of the head about an axis which is parallel to the aforementioned parallel pivot axes of/in the articulated arm (being a horizontal axis in the present embodiment) can remain constant the when the proximal arm section is pivoted or rotated relative to the support section and/or the distal arm section is pivoted or rotated relative to the intermediate linkage, whereby cross-angle is, advantageously, eliminated.

The proximal and distal arm sections and the intermediate linkage via which they are interconnected, advantageously define a collapsible elbow of the arm, whereby the articulated arm can assume a collapsed condition, in which the proximal and distal arm sections are positioned, in generally side-by-side relation, and an extended condition, in which the proximal and distal arm sections are positioned in generally coaxial relation and the intermediate linkage contributes to the reach of the articulated arm.

While various embodiments of the present invention have been described above, it should be understood that they have been presented by way of example only, and not by way of limitation. It will be apparent to a person skilled in the relevant art that various changes in form and detail can be made therein without departing from the spirit and scope of the invention. Thus, the present invention should not be limited by any of the above described exemplary embodiments.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A mobile radiographic imaging apparatus comprising:
a body section;
ground-engaging wheels arranged to support the body section over a floor surface and permitting maneuvering of the apparatus over the surface;
a component operable to emit X-ray radiation for imaging a subject;
an arm rotatably connected at a proximal end thereof to the body section, such that it is supported by the body section and can slew relative to the body section about an upright axis, and to a distal end of which said component is connected so as to be supported from the body section via said arm at a position which is radially offset from the upright axis in a first direction;
a generator assembly arranged in the body section, the assembly including a generator arranged in a casing and electrically connected to said component in order to supply power to said component for generation of the X-ray radiation; and
a slew bearing having a fixed part mounted to the body section and a rotatable part to which the arm is mounted so as to be able to slew about said upright axis, wherein the generator assembly is coupled to said rotatable part such that the generator assembly rotates with the arm, about said upright axis, during slewing of the arm,
wherein the generator assembly has a center of mass which is radially offset from said upright axis in a second direction that is substantially opposite to said first direction, so as to counteract a moment exerted on the body section by said arm and said component.

2. The apparatus according to claim 1, wherein the generator includes a tank of oil having a center of mass which is radially offset from said upright axis in said second direction.

3. The apparatus according to claim 1, including electrical cabling and/or other componentry housed by said casing.

4. The apparatus according to claim 1, wherein the generator assembly is housed by the body section.

5. The apparatus according to claim 1, wherein the generator assembly hangs or depends from the proximal end of the arm.

6. The apparatus according to claim 1, wherein the generator assembly is coupled to said rotatable part such that most or all of the weight of the generator assembly is transferred through the slew bearing into the body section.

7. The apparatus according to claim 1, wherein the arm is an articulated arm comprising a proximal arm section and a distal arm section to which the component is connected, and the arm is configured to articulate about an axis which is perpendicular to the upright axis, whereby a translational position of the component relative to the body section is adjustable.

* * * * *